(12) United States Patent
Flentov et al.

(10) Patent No.: US 7,054,784 B2
(45) Date of Patent: May 30, 2006

(54) SPORT MONITORING SYSTEMS

(75) Inventors: Peter Flentov, Carlisle, MA (US); Dennis M. Darcy, Dracut, MA (US); Curtis A. Vock, Boulder, CO (US)

(73) Assignee: PhatRat Technology, Inc., Niwot, CO (US)

( * ) Notice: Subject to any disclaimer, the term of this patent is extended or adjusted under 35 U.S.C. 154(b) by 0 days.

(21) Appl. No.: 10/950,897

(22) Filed: Sep. 27, 2004

(65) Prior Publication Data
US 2005/0038626 A1 Feb. 17, 2005

Related U.S. Application Data

(60) Division of application No. 10/234,660, filed on Sep. 4, 2002, now Pat. No. 6,856,934, which is a continuation of application No. 09/886,578, filed on Jun. 21, 2001, now Pat. No. 6,498,994, which is a continuation of application No. 08/867,083, filed on Jun. 2, 1997, now Pat. No. 6,266,623, which is a continuation-in-part of application No. 08/344,485, filed on Nov. 21, 1994, now Pat. No. 5,636,146.

(51) Int. Cl.
*G01P 11/00* (2006.01)

(52) U.S. Cl. ..................... 702/149; 342/104
(58) Field of Classification Search ............... 702/149, 702/153, 94–97, 142, 143, 150–152, 160, 702/188; 342/104–109, 357.06–14, 357.17, 342/450, 451, 458, 460, 113
See application file for complete search history.

(56) References Cited

U.S. PATENT DOCUMENTS

| | | | |
|---|---|---|---|
| 3,978,725 A | 9/1976 | Hadtke | |
| 4,089,057 A | 5/1978 | Eriksson | |
| 4,223,211 A * | 9/1980 | Allsen et al. | 377/24.2 |
| 4,371,945 A | 2/1983 | Karr et al. | |
| 4,578,769 A | 3/1986 | Frederick | |
| 4,694,694 A | 9/1987 | Vlakancic et al. | |
| 4,722,222 A | 2/1988 | Purdy et al. | |
| 4,757,714 A | 7/1988 | Purdy et al. | |
| 4,763,284 A | 8/1988 | Carlin | |
| 4,774,679 A | 9/1988 | Carlin | |
| 4,935,887 A | 6/1990 | Abdalah et al. | |
| 5,295,085 A | 3/1994 | Hoffacker | |
| 5,343,445 A | 8/1994 | Cherdak | |
| 5,452,269 A | 9/1995 | Cherdak | |
| 5,485,402 A * | 1/1996 | Smith et al. | 702/160 |
| 5,513,854 A | 5/1996 | Daver | |
| 5,583,776 A * | 12/1996 | Levi et al. | 701/217 |
| 5,636,146 A | 6/1997 | Flentov et al. | |
| 5,925,001 A * | 7/1999 | Hoyt et al. | 600/595 |
| 5,955,667 A | 9/1999 | Fyfe | |
| 6,020,851 A | 2/2000 | Busack | |
| 6,305,221 B1 * | 10/2001 | Hutchings | 73/488 |
| 6,619,835 B1 * | 9/2003 | Kita | 368/281 |
| 2002/0077784 A1 | 6/2002 | Vock et al. | |

OTHER PUBLICATIONS

Complaint, Civil Action 05-CV-02323.

* cited by examiner

*Primary Examiner*—Edward Raymond
(74) *Attorney, Agent, or Firm*—Lathrop & Gage LC

(57) ABSTRACT

Methods and systems are disclosed for determining speed, power and/or impact (sporting characteristics) of persons involved in activity. Wireless signals may be generated indicative of the sporting characteristics for receipt and display on a watch worn by the user or on a remote display. Sensors may attach to the person or to a vehicle ridden by the person, to gauge activities such as jogging, hockey, biking, football and aerobics.

10 Claims, 24 Drawing Sheets

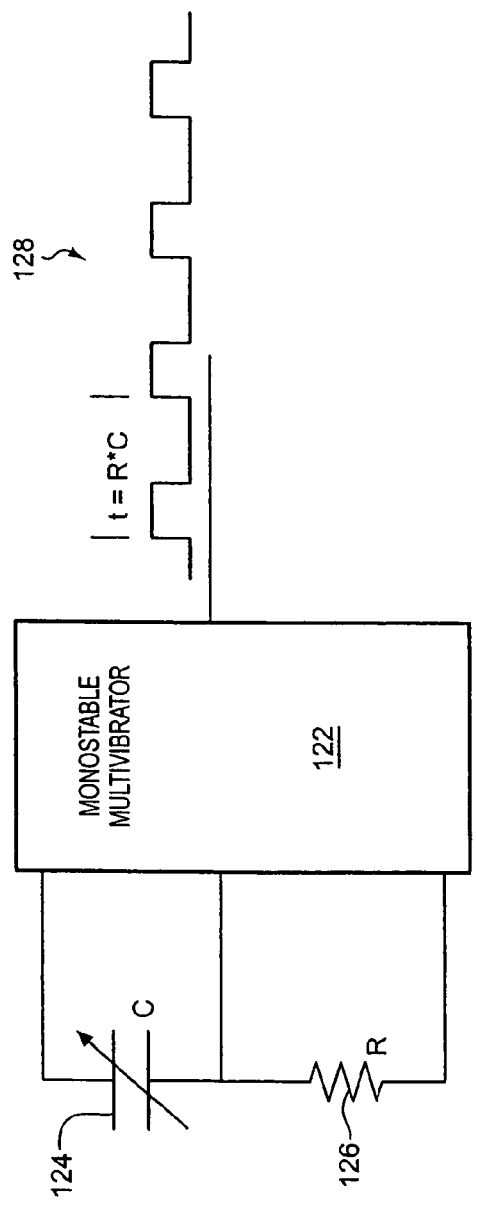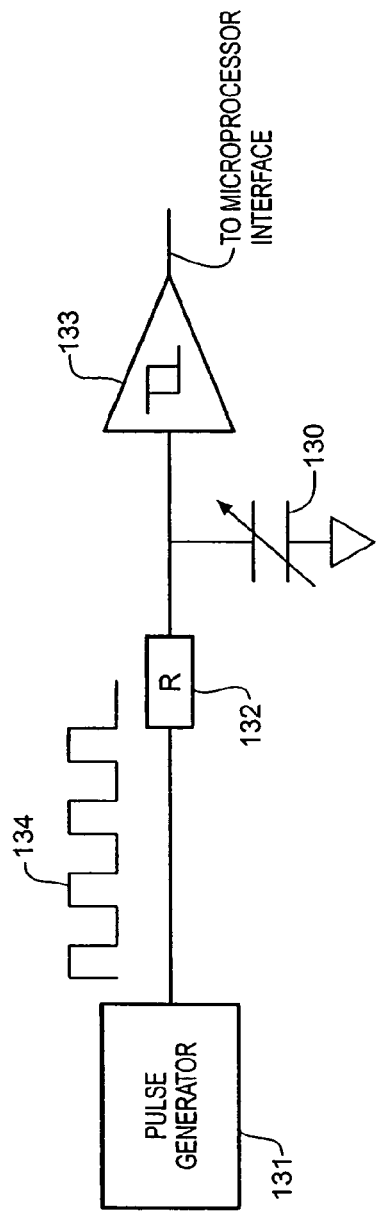

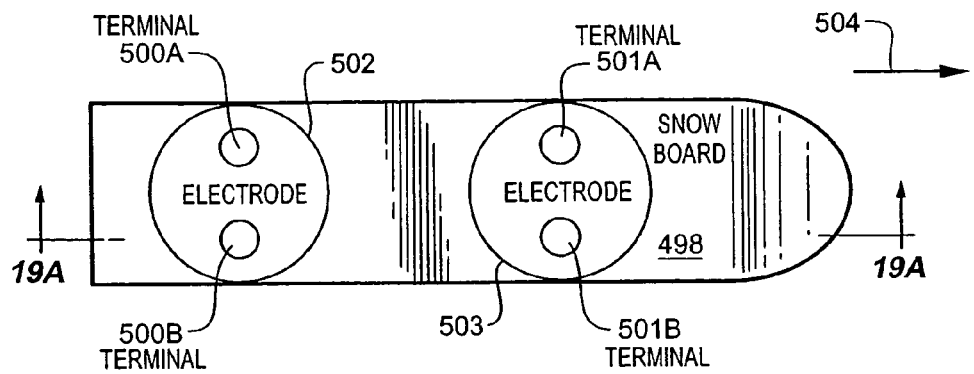
FIG. 19
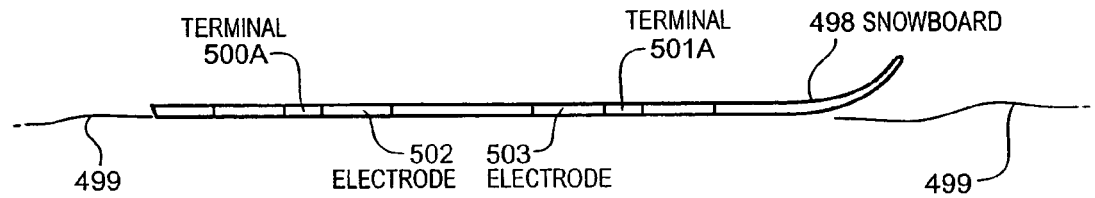
FIG. 19A
FIG. 19B
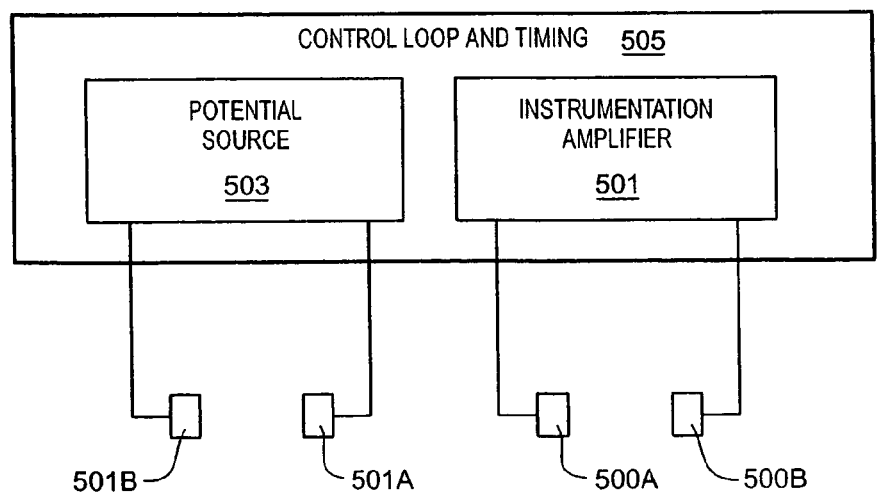

SPORT MONITORING SYSTEMS

RELATED APPLICATIONS

This application is a divisional of U.S. patent application Ser. No. 10/234,660, filed Sep. 4, 2002 now U.S. Pat. No. 6,586,934, which is a continuation of U.S. application Ser. No. 09/886,578, filed on Jun. 21, 2001 (now U.S. Pat. No. 6,498,994) and entitled Systems and Methods for Determining Energy Experienced by a User and Associated with Activity, which is a continuation of U.S. application Ser. No. 08/867,083, filed on Jun. 2, 1997 (now U.S. Pat. No. 6,266,623) and entitled Sport Monitoring Apparatus for Determining Loft Time, Speed, Power Absorbed and Other Factors Such as Height, which is a continuation-in-part of U.S. application Ser. No. 08/344,485 filed on Nov. 21, 1994 (now U.S. Pat. No. 5,636,146) and entitled Apparatus and Methods for Determining Loft Time and Speed, each of which are hereby incorporated by reference.

FIELD OF THE INVENTION

The invention relates generally measurement and/or sporting characteristics of speed and impact of moving persons. Such measurements and sporting characteristics may be recorded and/or presented to such persons via a watch or other remote display. Sensors may attach to persons or to vehicles ridden by such persons in a range of activities, including jogging, biking, hockey, aerobics and football.

BACKGROUND OF THE INVENTION

It is well known that many skiers enjoy high speeds and jumping motions while traveling down the slope. High speeds refer to the greater and greater velocities which skiers attempt in navigating the slope successfully (and sometimes unsuccessfully). The jumping motions, on the other hand, include movements which loft the skier into the air. Generally, the greater the skier's speed, the higher the skier's loft into the air.

The interest in high speed skiing is apparent simply by observing the velocity of skiers descending the mountain. The interest in the loft motion is less apparent; although it is known that certain enthusiastic skiers regularly exclaim "let's catch some air" and other assorted remarks when referring to the amount and altitude of the lofting motion.

The sensations of speed and jumping are also readily achieved in other sporting activities, such as in mountain biking. Many mountain bikers, like the aforementioned skiers, also crave greater speeds and "air" time.

However, persons in such sporting activities typically only have a qualitative sense as to speed and loft or "air" time. For example, a typical snowboarding person might regularly exclaim after a jump that she "caught" some "big sky," "big air" or "phat air" without ever quantitatively knowing how much time really elapsed in the air.

There are also other factors that persons sometimes assess qualitatively. For example, suppose a snowboarder goes down a double-diamond ski slope while a friend goes down a green, easy slope. When they both reach the bottom, the double-diamond snowboarder will have expended more energy than the other, generally, and will have worked up a sweat; while the green snowboarder will have had a relatively inactive ride down the slope. Currently, they cannot quantitatively compare how rough their journeys were relative to one another.

It is, accordingly, an object of the invention to provide apparatus and methods for determining the "air" time of participants in sporting activities such as skiing and mountain biking.

It is another object of the invention to provide apparatus and methods for determining the speed of participants in sporting activities such as skiing and mountain biking.

It is yet another object of the invention to provide improvements to sporting devices which are ridden by sporting participants, and which provide a determination of speed and/or loft time of the device.

Still another object of the invention is to provide apparatus and methods for determining the amount of "power" or energy absorbed by a person during sporting activities.

These and other objects of the invention will become apparent in the description which follows.

SUMMARY OF THE INVENTION

The following U.S. patents provide useful background for the Invention and are herein incorporated by reference: U.S. Pat. No. 5,343,445; U.S. Pat. No. 4,371,945; U.S. Pat. No. 4,757,714; U.S. Pat. No. 4,089,057; U.S. Pat. No. 3,978,725; and U.S. Pat. No. 5,295,085.

The invention concerns the detection and display of loft, or "air" time and/or speed of vehicles such as sporting vehicles, including skis, bikes, and snowboards. The invention thus provides a visual and quantitative measure of how much "air" time and, in certain aspects, how fast a user moves in a particular activity.

The invention provides, in one aspect, apparatus for determining the loft time of a moving vehicle off of a surface. A loft sensor senses a first condition that is indicative of the vehicle leaving the surface, and further senses a second condition indicative of the vehicle returning to the surface. A microprocessor subsystem, e.g., a microcontroller, determines a loft time that is based upon the first and second conditions, and the loft time is thereafter displayed to a user of the apparatus by a display, e.g., a LCD or LED display. Preferably, a power module such as a battery is included in the apparatus to power the several components. In addition, a housing preferably connects and protects the microprocessor subsystem and the user interface; and further such that the housing is attachable to the vehicle.

According to another aspect, the invention includes memory for storing information representative of at least one of the following: (i) the first and second conditions, (ii) the loft time, (iii) a speed of the vehicle, (iv) successive records of loft time, (v) an average loft time, (vi) a total loft time, (vii) a dead time, (viii) a real activity time, and (ix) a numerical ranking of successive records.

One preferred aspect of the invention includes a speed sensor, connected to the microprocessor subsystem, which senses a third condition that is indicative of a velocity of the vehicle. In this aspect, the microprocessor subsystem includes means for converting the third condition to information representative of a speed of the vehicle. Accordingly, the apparatus provides a user with both loft time, e.g., "air" time, and a speed of the vehicle.

In yet another aspect, the display of the invention can display selective information, including one or more of the following: the loft time; a speed of the vehicle; a peak loft time; an average loft time; a total loft time; a dead time; a real activity time; an average speed; an indication that loft time is being displayed; an indication that speed is being displayed; an indication that dead time is being displayed; an indication that real activity time is being displayed; successive records of loft information; successive records of speed information; a distance traveled by the vehicle; a height achieved by the vehicle off of the surface; and an indication of a number of a successive record relative to all successive records.

In still another aspect, the invention includes a user interface for providing external inputs to the apparatus, including one or more of the following: a start/stop button for selectively starting and stopping the acquisition of data by the apparatus; a display-operate button for activating the display means selectively; a speed/loft toggle button for alternatively commanding a display of loft time information and speed information of the vehicle; means for commanding a display of successive records of loft time information selectively; means for commanding a display of successive records of speed information selectively; means for commanding a display of information corresponding to average loft time; means for commanding a display of information corresponding to average speed; means for commanding a display of total loft time; means for commanding a display of dead time; means for commanding a display of distance traveled by the vehicle; means for commanding a display of height achieved by the vehicle off of the surface; and means for commanding a display of real activity time.

Preferably, the microprocessor subsystem of the invention includes a dock element, e.g., a 24-hour clock, for providing information convertible to an elapsed time. Accordingly, the subsystem can perform various calculations, e.g., dead time, on the data acquired by the apparatus for display to a user.

In another aspect, the loft sensor is constructed with one of the following technologies: (i) an accelerometer that senses a vibrational spectrum; (ii) a microphone assembly that senses a noise spectrum; (iii) a switch that is responsive to a weight of a user of the vehicle; (iv) a voltage-resistance sensor that generates a voltage indicative of a speed of the vehicle; and (v) a plurality of accelerometers connected for evaluating a speed of the vehicle.

In a preferred aspect, the loft sensor of the invention senses a spectrum of information, e.g., a vibrational or sound spectrum, and the microprocessor subsystem determines the first and second conditions relative to a change in the spectrum of information. Further, the microprocessor subassembly interprets the change in the spectrum to determine the loft time.

For example, one aspect of a loft sensor according to the invention includes one or more accelerometers that generate a vibrational spectrum of the vehicle. In such an aspect, the first and second conditions correspond to a change in the vibrational spectrum. By way of another example, one loft sensor of the invention includes a microphone subassembly that generates a noise spectrum of the vehicle; and, in this aspect, the first and second conditions correspond to a change in the detected noise spectrum. Because these spectrums are influenced by the particular activity of a user, e.g., standing in a ski line, a microprocessor subsystem of the invention preferably includes means for assessing boundary conditions of the spectrum and for excluding certain conditions from the determination of loft time. Accordingly, if a skier is in a lift line, such conditions are effectively ignored. One boundary condition, therefore, according to an aspect of the invention, includes an elapsed time between the first condition and the second condition that is less than approximately 500 ms; such that events that are within this boundary condition are excluded from the determination of loft time. One other boundary condition, in another aspect, includes an elapsed time between the first condition and the second condition that is greater than approximately five seconds; such that events that are outside this boundary condition are excluded from the determination of loft time. Because these boundary conditions are important in the aspects of the invention which utilize a spectrum of information, the apparatus preferably utilizes a user interface for providing selective external inputs to the microprocessor subsystem and for adjusting the boundary conditions selectively.

In still another aspect of the invention, the microprocessor subassembly includes means for determining a pitch of the spectrum by determining a best-fit sine wave to a primary frequency of at least part of the spectrum and means for correlating the pitch to a vehicle speed. Accordingly, the invention can detect spectrum information and correlate that information to a speed of the vehicle. Typically, a higher pitch frequency corresponds to a higher vehicle speed and a lower pitch frequency corresponds to a lower vehicle speed. However, in another aspect, the selected pitch frequency can be calibrated relative to a selected vehicle and speed.

The invention also provides, in another aspect, means for storing information including look-up tables with pitch-to-speed conversions for a plurality of vehicles. This is useful because different vehicles have different associated noise and/or sound spectrums associated with the vehicle. Accordingly, the invention in this aspect includes memory for storing the respective calibration information of the different vehicles (typically in a look-up table format) so that a user can utilize the invention on different vehicles and still determine speed accurately. Specifically, a particular pitch is associated with a particular speed for a particular vehicle; and that association is selectively made by the user.

The vehicles which are preferably used, according to the invention, include (i) a snowboards, (ii) snow skis, (iii) water skis, (iv) skis for ski jumping, and (v) skis for ski flying. However, in certain aspects of the invention, a human vehicle can be used; although the processing power required to accurately process speed and/or loft information in this aspect is significantly increased.

In several aspects of the invention, the microprocessor subassembly includes one or more of the following: means for selectively starting and stopping the acquisition of data by the apparatus; means for responding to an external request to activate the display means; means for responding to an external request to alternatively display the loft time and a speed of the vehicle; means for calculating a speed of the vehicle; means for responding to an external request to display successive records of loft time information; means for responding to an external request to display successive records of speed information; means for determining an average speed; means for determining a total loft time; means for determining a dead time; means for responding to an external request to display information corresponding to an average loft time; means for responding to an external request to display information corresponding to an average speed; means for responding to an external request to display a total loft time; means for responding to an external request to display a dead time; means for responding to an external request to display a distance traveled by the vehicle; means for responding to an external request to display a height achieved by the vehicle off of the surface; and means for responding to an external request to display a real activity time.

The invention also provides certain improvements to sporting vehicles of the type ridden by a user on a surface (e.g., sporting vehicle such as (i) snowboards, (ii) snow skis, (iii) water skis, (iv) skis for ski jumping, and (v) skis for ski flying). The improvements include, in one aspect, a speed sensor having (i) a voltage-measuring circuit including a pair of conductors arranged to contact the surface so that the surface is part of the circuit, and (ii) an electromagnet for selectively generating a magnetic field on the circuit, wherein a voltage generated by the circuit is proportional to a speed of the vehicle. In such an aspect, the microprocessor subsystem determines a speed of the vehicle that is based upon the voltage, and that speed is displayed to a user.

The invention also provides certain methodologies. For example, in one aspect, the invention provides a method for determining the loft time of a moving vehicle off of a surface, comprising the steps of: (1) sensing the vehicle leaving the surface at a first time; (2) sensing the vehicle returning to the surface at a second time; (3) determining a loft time from the first and second times, and (4) displaying the loft time to a user of the apparatus.

In still anther aspect, the invention provides a method of measuring the amount of "power" a user absorbs during the day. A motion sensor, e.g., a microphone or accelerometer, attaches to the vehicle, preferably pointing perpendicular to the top of the vehicle (e.g., perpendicular to the top surface of the snowboard) so that a measure of acceleration or "force" jarring the user can be made. The data from the motion sensor is integrated over a selected time—e.g., over the time of the skiing day—so that an integrated measure of motion is acquired. By way of example, if the motion sensor is an accelerometer positioned with a sensitive axis arranged perpendicular to the top snowboard surface, then, through integration, an integrated measure of "power" is obtained.

Those skilled in the art should appreciate that the measure can be converted to actual power or similar units—e.g., watts or joules or ergs or Newtons—though the actual unit is not as important as having a constant, calibrated measure of "power" for each user. That is, suppose two snowboarders have such motion sensors on their respective snowboards. If one person goes down a green slope and another down a double-diamond, then the integrated value out of the double-diamond snowboarder will be greater. The units are therefore set to a reasonably useful value, e.g., generic power "UNITS." In one aspect, the power units are set such that a value of "100" indicates a typical snowboarder who skies eight hours per day and on maximum difficult terrain. At the same time, a snowboarder who rides nothing but green beginner slopes, all day, achieves something far less, e.g., a value of "1". In this manner, average skiers on blue, intermediate slops will achieve intermediate values, e.g., "20" to "50". Other scales and units are of course within the scope of the invention.

The measure of power according to the invention thus provides significant usefulness in comparing how strenuous one user is to another. For example, suppose two users ski only blue, intermediate slopes with the exact same skill and aggressiveness except that one user chooses to sit in the bar for three hours having a couple of cocktails. At the end of an eight hour day—providing the power sensor is activated for the whole day—the skier who skied all eight hours will have a power measurement that is 8/5 that of his cocktail-drinking companion. They can thereafter quantitatively talk about how easy or how difficult their ski day was. As for another example, suppose a third friend skis only double-diamond slopes and he takes four hours out to drink beer. At the end of the day, his power measure may still be greater than his friends depending upon how hard he skied during his active time. He could therefore boast—with quantitative power data to back him up—that he had more exercise than either of his friends even though he was drinking half the day.

The measure of air time, according to the invention, can also be used in a negative sense. That is, speed skiers try to maintain contact with the ground as air time decreases their speed. By monitoring their air time with the invention, they are better able to assess their maneuvers through certain terrain so as to better maintain ground contact, thereby increasing their time.

The measurement of air, speed and power, in accord with the invention, is preferably made via a sensor located on the vehicle, e.g., on the snowboard or ski on which the person rides. As such, it is difficult to see the sensor; so in one aspect the invention provides an RF transmitter in the sensor and a watch, with an RF receiver, located on the wrist of the person. The data—e.g., air, power and speed—is transmitted to the person for easy viewing on the watch. In still other aspects, a memory element in the watch provides for storing selected parameters such as successive records of speed, air and power, or the average "power" spent during the day.

The invention is next described further in connection with preferred embodiments, and it will be apparent that various additions, subtractions, and modifications can be made by those skilled in the art without departing from the scope of the invention

BRIEF DESCRIPTION OF THE DRAWINGS

A more complete understanding of the invention may be obtained by reference to the drawings, in which:

FIG. 8 schematically illustrates electronics, constructed according to the invention, for converting a varying capacitance, e.g., the capacitance derived from the loft sensor of FIG. 7, to information suitable for calculating "air" time;

FIG. 9 schematically illustrates alternative electronics, constructed according to the invention, for converting a varying capacitance, e.g., the capacitance derived from the loft sensor of FIG. 7, to information suitable for calculating "air" time;

FIGS. 19 and 19A show one embodiment of the invention for determining speed through charge cookies; and FIG. 19B shows a circuit for coupling with the apparatus of FIGS. 19 and 19A;

DETAILED DESCRIPTION OF ILLUSTRATED EMBODIMENTS

Figure 1:
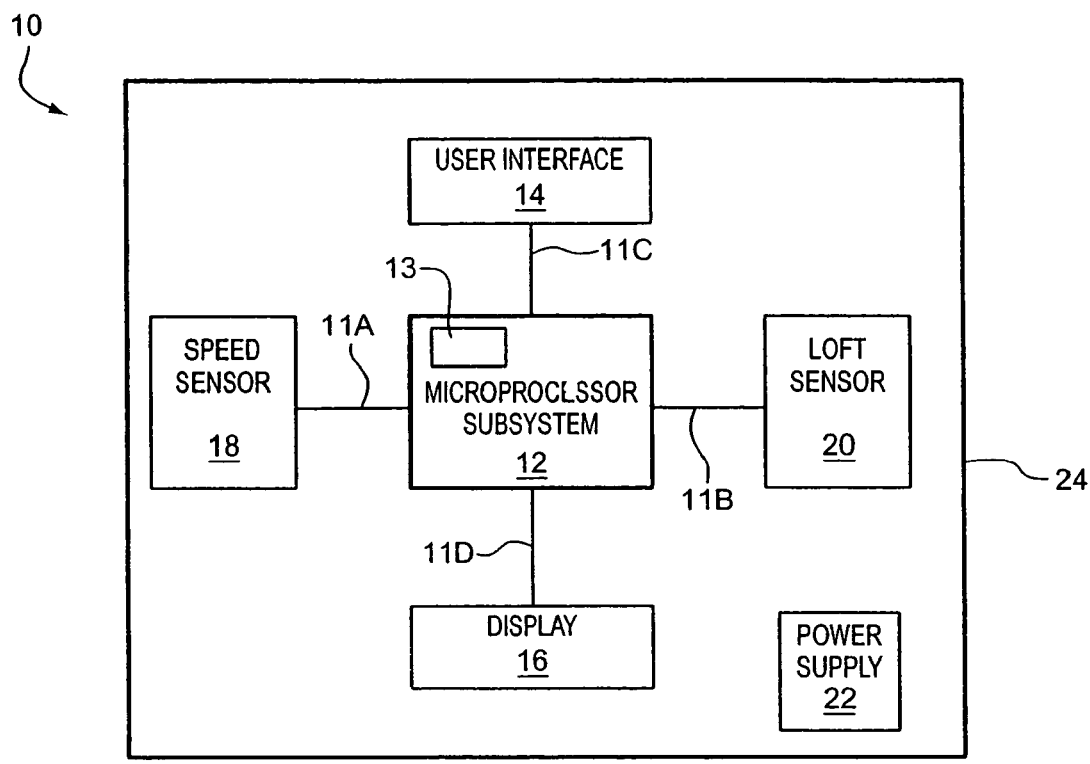
FIG. 1 illustrates a system constructed according to the invention for determining loft and speed of a sporting vehicle carrying the system.

FIG. 1 illustrates a system 10 constructed according to the invention. A microprocessor subsystem 12 controls the system 10 and connects to a user interface 14, a display 16, speed sensor 18 and loft sensor 20. A power supply 22, e.g., a battery, provides power to the system 10 and connects to the components 12, 14, 16, 18 and 20 via appropriate electrical interconnections (not shown). The microprocessor subsystem 12 includes memory 13 for storing data acquired by the system 10.

The system 10 is incorporated into a relatively small housing, shown by the outline 24. The housing 24 is preferably arranged to protect the components 12, 14, 16, 18 and 20 from the elements of nature—such as rain, snow, sand and dust, each of which is expected during the ordinary course of usage on a ski slope and/or mountain bike trail. In addition, the housing 24 is attachable to a vehicle, such as a ski or mountain bike, by means such as a glue or a mechanical mount, e.g., screws. Alternatively, the housing (and hence the system 10) is incorporated integrally with the vehicle, such as inside a ski, such that only the display 16 and user interface 14 are visible and accessible.

Briefly, the invention shown in FIG. 1 operates as follows. The housing 24 is attached or mounted to a sporting device, such as a ski or mountain bike, such that a user of the ski or mountain bike can access the system 10. During motion of the ski or mountain bike, the speed sensor 18 sends velocity information (over communication line 11a) to the microprocessor subsystem 12; while the loft sensor 20 sends loft or "air" time information (over communication line 11b) to the microprocessor subsystem 12. The speed information and loft time information are processed by the microprocessor subsystem 12 to quantify actual speed, e.g., in miles per hour, and actual loft time, e.g., in seconds. The actual speed and loft time are thereafter stored in internal memory 13 until, at least, the speed and time data are accessed by a user of the system 10. Upon access through the user interface 14 (communicating with the microprocessor subsystem 12 via communication line 11c), a user of the system 10 can command the display of the speed and loft time data (sent across communication line 11d) on the display 16 in order to evaluate his or her performance in the sporting activity.

In an alternative embodiment, the speed and loft information can be stored prior to processing by the microprocessor subsystem 12; and later post-processed for display on the display 16 when commanded by a user of the system 10. Such an embodiment may be useful to conserve energy and to perform calculations to quantify the speed and loft data in a "batch" mode, such as known to those skilled in the art.

The system 10 of FIG. 1 preferably includes both of the speed sensor 18 and loft sensor 20; although it is not necessary for both sensors to be present in accord with the invention. Rather, in certain embodiments of the invention, only the loft sensor 20 is present within the system 10; and in certain other embodiments of the invention, only the speed sensor 18 is present within the system 10. Accordingly, in these embodiments, only the loft data or speed data, respectively, are available to a user of the system because the sensor which measures the information is absent.

Figure 2:
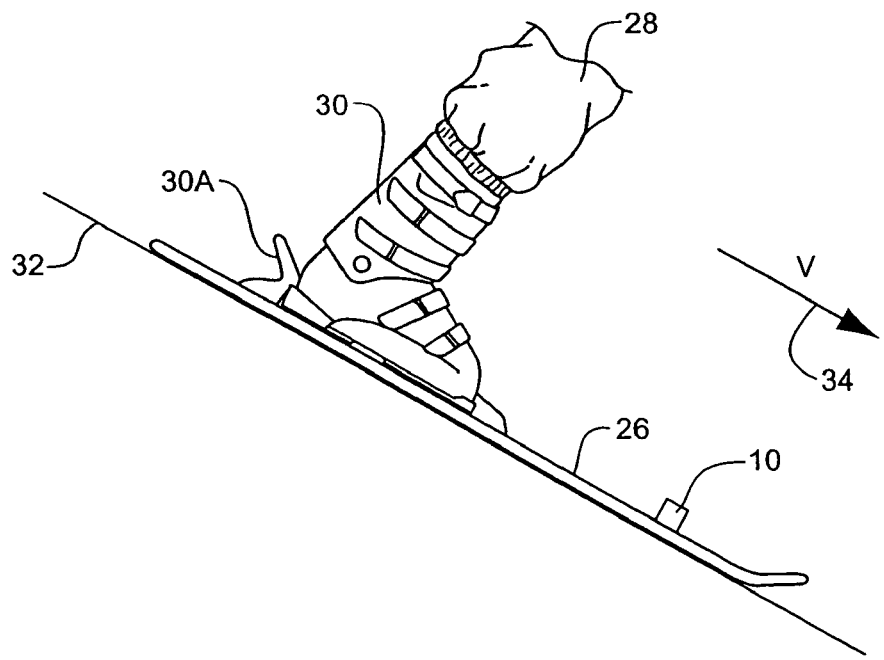
FIGS. 2, 2A and 2B show illustrative uses for the system 10 shown in FIG. 1.
Figure 2A:
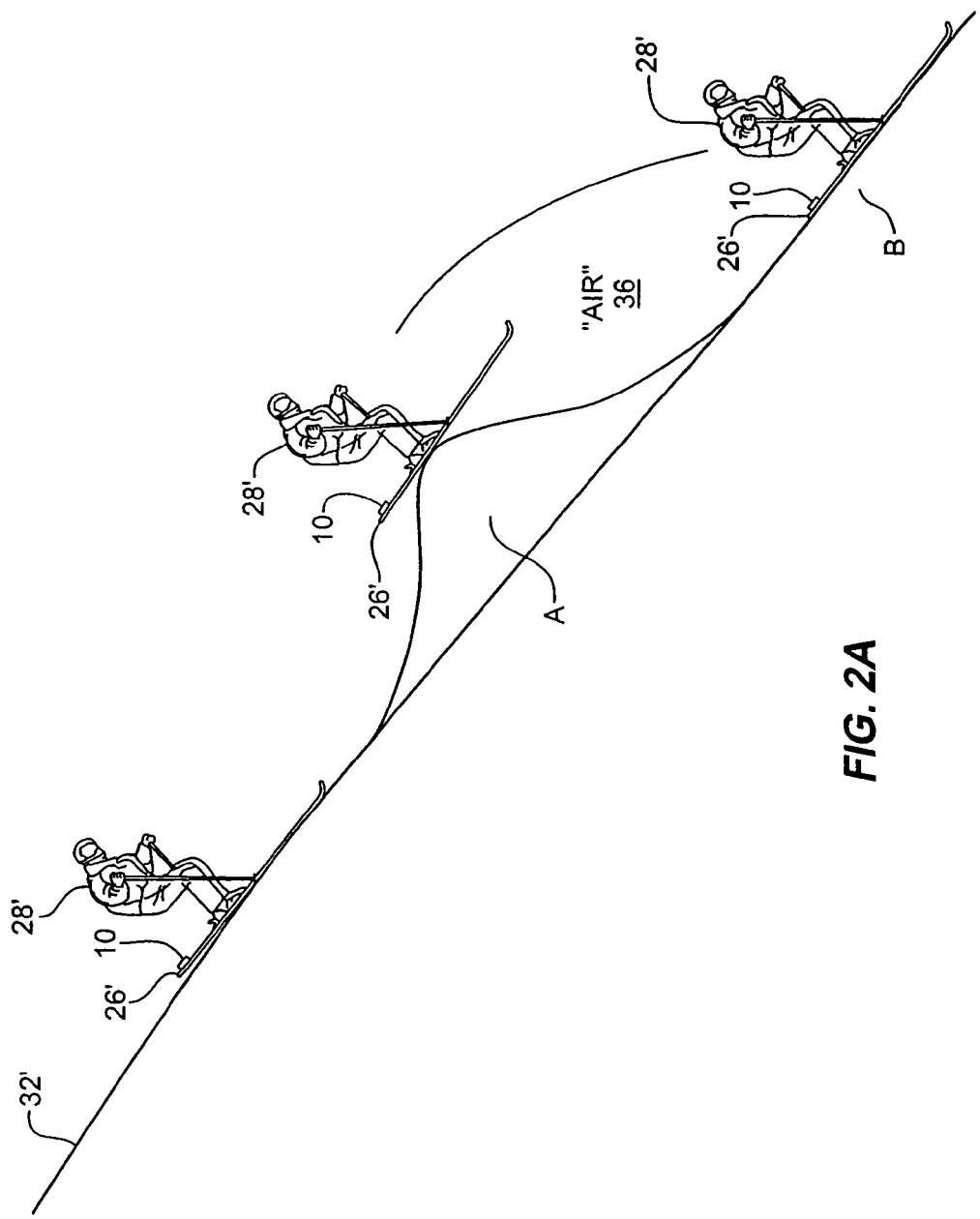
Figure 2B:
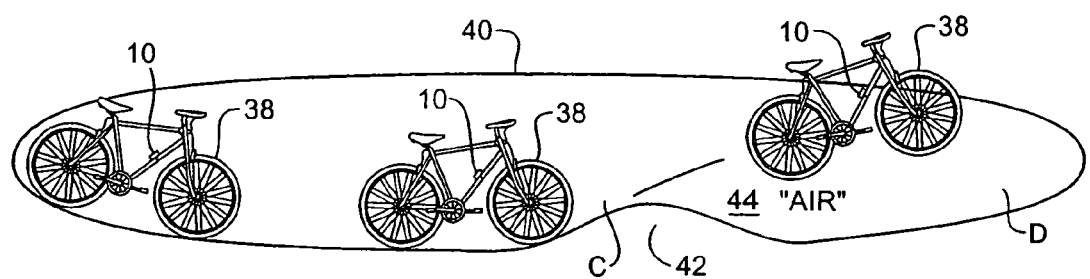

FIGS. 2, 2A and 2B show typical uses of the system 10 illustrated in FIG. 1. In particular, FIG. 2 shows the system 10 mounted onto a ski 26. As is normal, the ski 26 is mounted to a skier 28 (for illustrative purposes, the skier 28 is only partially illustrated), via a ski boot 30 and binding 30a, and generally descends down a ski slope 32 with a velocity 34. Accordingly, one use of the system 10 is to calculate the peak speed of the ski 26 (and hence the skier 28) over a selectable period of time, e.g., during the time of descent down the slope 32.

Another use of the system 10 of FIG. 1 is to calculate the loft, or "air" time of the ski 26 (and hence the user 28) during the descent down the slope 32. Consider, for example, FIG. 2A, which illustrates the positions of the ski 26' and skier 28' during a lofting maneuver on the slope 32'. The ski 26' and skier 28' speed down the slope 32' and launch into the air 36 at position "a," and later land at position "b" in accord with the well-known Newtonian laws of physics. The system 10 calculates and stores the total "air" time that the ski 26' (and hence the skier 28') experience between the positions "a" and "b" so that the skier 28' can access and assess the "air" time information.

FIG. 2B illustrates the system 10 mounted onto a mountain bike 38. FIG. 2B also shows the mountain bike 38 in various positions during movement along a mountain bike race course 40 (for illustrative purposes, the bike 38 is shown without a rider). At one location "c" on the race course 40, the bike 38 hits a dirt mound 42 and catapults into the air 44. The bike 38 thereafter lands at location "d." As above, the system 10 provides information to a rider of the bike 38 about the speed attained during the ride around the race course 40; as well as information about the "air" time between location "c" and "d."

User Interface and Display

With further reference to FIG. 1, the display 16 can be one of any assortment of displays known to those skilled in the art. For example, liquid crystal displays (LCDs) are referred because of their low power draw (for example, LCDs utilized in digital watches and portable computers are appropriate for use with the invention). Other suitable displays can include an array of light emitting diodes (LEDs) arranged to display numbers.

Figure 3:
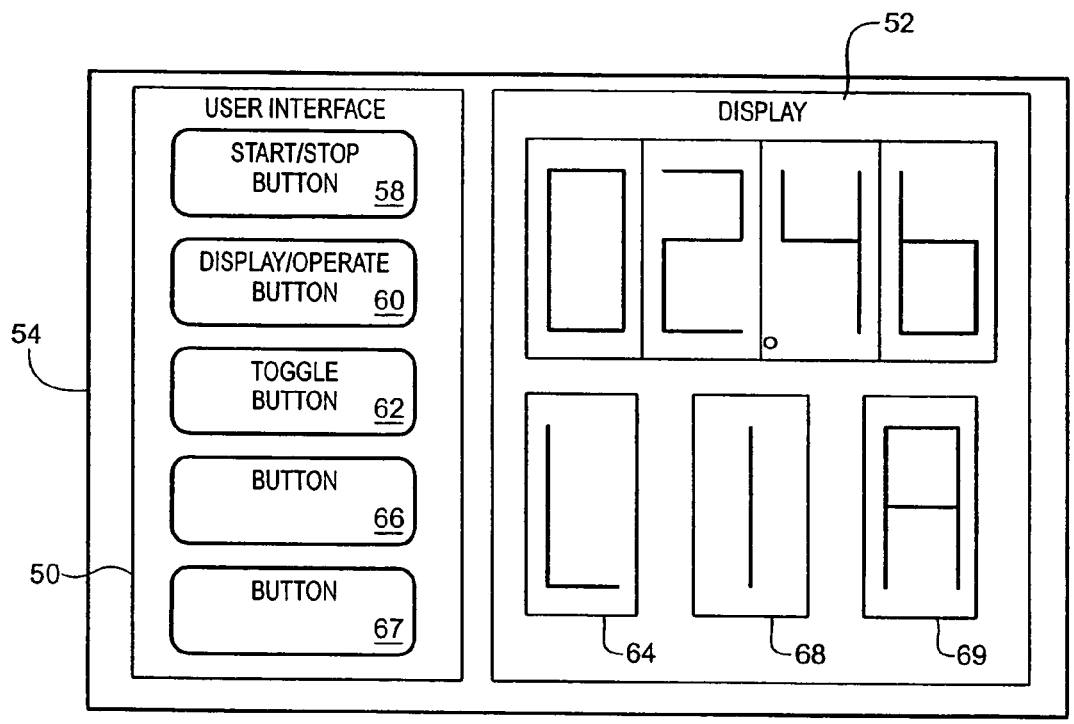
FIG. 3 illustrates a user interface and display suitable for use in the system of FIG. 1.

FIG. 3 illustrates a user interface 50 and display 52 constructed according to the invention and which are suitable for use, respectively, as the interface 14 and display 16 of FIG. 1. Outline 54 illustrates the outline of a system constructed according to the invention, e.g., the housing outline 24 of the system 10 of FIG. 1. In order for a user of the system to access information within the system, user interface 50 includes control buttons. For example, with reference to FIG. 3, one embodiment of the user interface 50 includes a start/stop button 58, a display-operate button 60, and a speed/loft toggle button 62. These buttons operate as follows:

A user presses the start/stop button 58 at the start of activity—such as at the start of skiing down a slope or biking down a trail—and presses the button 58 at the completion of activity to cease the acquisition of data (as described in more detail below).

A user pressed the display-operate button 60 to activate the display 52 so that a user can view recorded information from the sporting activity on the display 52. Accordingly, the display 52 is normally OFF—and not drawing power from the associated power source (e.g., the power source 22 of FIG. 1)—and is turned ON only when a user activates the display-operate button 52. The ON and OFF display conditions are preferably obtained in one of two ways: in one embodiment of the invention, the display 52 automatically turns OFF after a preselected time through the control of the microprocessor subsystem 12 of FIG. 1; or, in an alternative embodiment, the display 52 remains activated until a user again presses the display-operate button 60.

A user presses the speed/loft toggle button 62 to sequentially command the display, respectively, of information about speed and loft time. For example, if the display 52 currently displays speed information, a user can instead command the display of loft time information by pressing the speed/loft toggle button 62 once. If, on the other hand, the display 52 currently displays loft information, a user can instead command the display of speed information by pressing the speed/loft toggle button 62 once. Preferably, one portion 64 of the display denotes whether speed or loft information is being displayed. For example, as illustrated, a "L" letter denotes that loft information is being displayed. An "S" letter likewise denotes that speed information is being displayed. For illustrative purposes, the "air" time is also displayed in FIG. 3 as 2.46 seconds, which represents the "air" time of a typical ski jump.

It is important to note that one embodiment of the invention does not include the speed/loft toggle button 62 because, as noted earlier, certain embodiments of the invention do not include both the speed sensor and loft sensor. In such an embodiment, it is unnecessary to include a toggle button 62.

The display 52 of FIG. 3 also shows another feature of the invention, namely that a system constructed according to the invention preferably calculates and stores successive records relating to speed and loft information relative to a user's activity. For example, a skier may catch "air" time more than once during a given activity; and the system of the invention can store successive loft times for access by the user. Most often, the peak "air" time is displayed, by default. However, certain users wish to evaluate successive loft time information and, accordingly, the system 10 of FIG. 1 preferably determines and stores the successive information (described in greater detail below). A user can access the successive loft time information by toggling a combination of the buttons 58–62, such as known to those skilled in the art (e.g., a combination of holding one button down while pressing another button); or by including yet another button 66 on the user interface 50. A display portion 68 of the display 52 shows a number corresponding to the sequential information on display. For example, the illustrated "1" number means that the highest "air" time record is currently being displayed; while a number greater than one means that a loft time other than the highest loft time is being displayed. In addition, the highest number displayed within the portion 68 refers to the total number of "air" times for the selected activity period (thus for example a user can determine the total number of jumps achieved for a given day).

In still another embodiment of the invention, successive speed information can be displayed much the way successive "air" time information is stored and displayed, described above. To view the speed information, the speed/loft toggle button 62 is pressed once to display "S" in the display portion 64, and a user can toggle button 66 to view the successive speed records as denoted by the number in display portion 68. However, this information is not deemed very useful except under a very few circumstances—since a user generally moves with some velocity during a given activity—and thus, generally, the peak speed achieved during a given activity is normally displayed on the display 52 when commanded by the speed/loft toggle button 62.

In an alternative embodiment, a button 67 is used to alter the modes of the system so that other information such as average "air" time may be calculated and displayed by the invention. For example, FIG. 3 illustrates a display portion 69 that shows a letter "A," corresponding to information relating to averages. Thus, for a particular sporting activity, a user can press button 69 to display "air" time as a running average of all the successive "air" times (in such an embodiment, the display portion 68 is preferably OFF because the information displayed in portion 68 refers to successive peak information). To access the peak "air" time information, the button 67 is pressed once again, causing the microprocessor subsystem 12 to change the display information from integrated average values to peak values (accordingly, the display portion 69 preferably shows a "P" to identify to the user that peak information is being displayed; and the display portion 68 is preferably ON in this "peak" mode to denote which successive record is being displayed). To access integrated information—e.g., the total "air" time for a given day—the button 67 is pressed once again, causing the microprocessor subsystem 12 to show the integrated "air" or speed information (depending on the toggle of the speed/loft toggle button 62). Integrated values are preferably displayed by indicating to the user a "T" (for total) in the display portion 69.

It should be clear to those skilled in the art that other buttons and/or combinations of buttons can be incorporated within the user interface 50 within the scope of the invention. The microprocessor subsystem 12 of FIG. 1 stores much information during the sporting activity and which can be converted to different forms, e.g., averages, peaks, and totals. In accord with the invention, different buttons and combinations of buttons can be used to access all of the available information. In addition, other information can be denoted, for example, within the display portion 69 to identify the different types of information available within the system.

For example, yet another form of information which may be of interest to sporting persons is the "dead" time, i.e., the time that the person is not skiing or biking during the day. For example, a person who hangs out in the bar during part of the afternoon will not have a high efficiency factor for actual ski time as compared to the available ski time. This efficiency information is available in accord with the invention because the microprocessor subsystem 12 of FIG. 1 preferably includes a dock element (readily known to those skilled in the art) for indicating processed time over a selectable period (the microprocessor subsystem 12 can in fact include a 24-hour clock element, much the way a digital wrist-watch includes 24-hour information). Accordingly, a user can start the system 10 of FIG. 1 at the beginning of the day by pressing the start/stop button 58, and stop the collection of data at the end of the day by again pressing the start/stop button 58. The microprocessor subsystem 12 keeps track of the elapsed time between the start and stop of the system (i.e., the selectable time period), thereby providing means for determining the user's "dead" time for the day. That is, the microprocessor subsystem 12 calculates "dead" time by intelligently calculating the total time lapse within which a vibrational noise spectrum (described in more detail below in connection with FIG. 4) is present within the selectable time period; and dividing that total time lapse by the selectable time period to obtain a ratio of the real activity time versus the user's dead time (for example, a ratio of 80% means that the sporting person skied for 80% of the day). Dead time information is thereafter easily determined by subtracting 80% from 100%, to get 20% dead time. The dead time information is shown, for example, by toggling the button 67 to a dead time mode, denoted as "D," in the display portion 69, and displaying the dead time as a percentage in the display 52. Alternatively, the real activity time is displayed as a percentage in the display 52 by toggling the button 69 until "R" shows up in the display portion 69.

Loft Sensor

With further reference to FIG. 1, the loft sensor 20 may be constructed by several known components. Preferably, the sensor 20 is either an accelerometer or a microphone assembly. Alternatively, the sensor 20 may be constructed as a mechanical switch that detects the presence and absence of weight onto the switch. Each of these alternatives is described below.

Loft Sensor: Accelerometer Embodiment

An accelerometer, well known to those skilled in the art, detects acceleration and provides a voltage output that is proportional to the detected acceleration. Accordingly, the accelerometer senses vibration—particularly the vibration of a vehicle such as a ski or mountain bike—moving along a surface, e.g., a ski slope or mountain bike trail. This voltage output provides an acceleration spectrum over time; and information about loft time can be ascertained by performing calculations on that spectrum. Specifically, the microprocessor subsystem 12 of FIG. 1 stores the spectrum into memory 13 and processes the spectrum information to determine "air" time.

Figure 4:
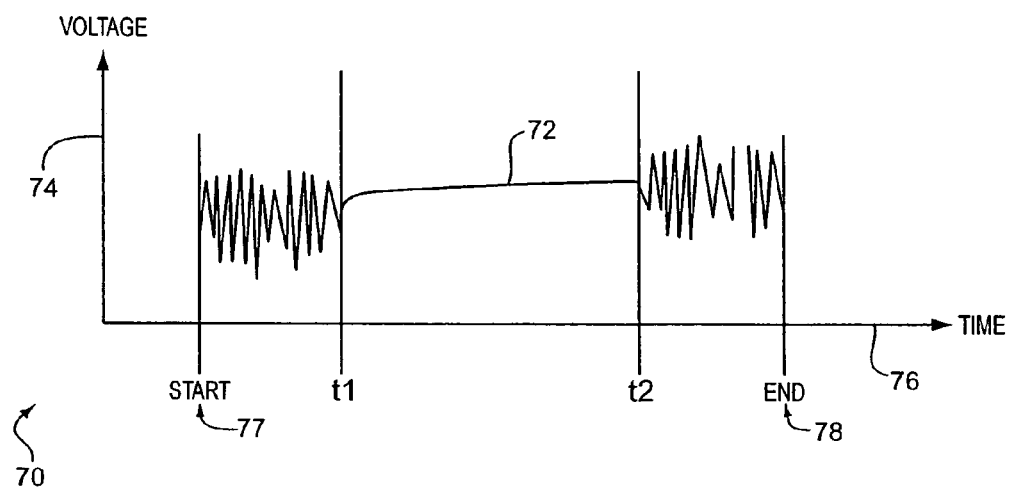
FIG. 4 is a representative vibrational spectrum, shown illustratively, for calculating "air" or loft time in accord with the invention.

FIG. 4 illustrates a graph 70 of a representative vibrational spectrum 72 that is stored into the microprocessor subsystem 12 (FIG. 1). The vertical axis 74 of the graph 70 represents voltage; while the horizontal axis 76 represents time. At the beginning of activity 77—such as when a user of a system constructed according to the invention presses the start/stop button 58 (see FIG. 3)—the loft sensor 20 of FIG. 1 begins acquiring data and transferring that data to the microprocessor subsystem 12 via communication lines 11*b*. This data appears highly erratic and random, corresponding to the randomness of the surface underneath the vehicle (e.g., ski or vehicle). At time "t1," the user of the system lofts into the air, such as illustrated as location "a" in FIG. 2A and as location "c" in FIG. 2B; and lands some time later at time "t2," such as illustrated as location "b" in FIG. 2A and as location "d" in FIG. 2B. The vibrational spectrum between t1 and t2 is comparatively smooth as compared to the spectrum outside this region because the user's sporting vehicle (e.g., the ski or mountain bike) is in the air and is not therefore subjected to the random vibrations of the road or ski slope. Accordingly, this relatively smooth spectrum between t1 and t2 can be readily discerned from the rest of the spectrum by the microprocessor subsystem 12 and evaluated for "air" time: specifically, "air" time is t2−t1.

FIG. 4 also shows that the spectrum stops at the end 78 of the sporting activity, such as when the user of the system again presses the start/stop button 58, FIG. 3.

In one embodiment of the invention, a user can simply start the system 10 of FIG. 1 at the beginning of the day, by toggling the start/stop button 58, and stop the system 10 at the end of the day, by again toggling the start/stop button 58. The issue here, however, is that there may be apparent "air" times between the starting and stopping of the system which is not, in fact, the "air" time of interest. For example, standing in line at a ski lift represents a period within which the spectrum 72 appears smooth, and might be mistaken for "air" time. Accordingly, the microprocessor subsystem 12 of the invention preferably includes process boundary conditions within which "air" time will be excluded. For example, one practical boundary condition is: if the spectrum between any given "t1" and "t2" time (FIG. 4) is greater than five seconds, then exclude that time from memory as actual "air" time. Thus, each time the skier stands in line, that smooth spectrum which is being processed by the system is ignored.

Another boundary condition, for example, concerns the type of skier using the system. Some skiers often make quick jump turns down the mountain. These would normally show up as mini "air" times. Thus, in accord with another aspect of the invention, another boundary condition is: if the spectrum between any given "t1" time and "t2" time (FIG. 4) is less than 500 ms, then exclude that time from memory as actual "air" time. Accordingly, each jump turn will not be included in the total "air" time for the day, as is expected by users of the system.

The invention preferably includes an adjustment mechanism to adjust these boundary conditions (e.g., the five seconds maximum and the 0.5 second minimum) so that such conditions can be adjusted and optimized to individual users. Accordingly, in one embodiment of the invention, certain of the buttons 58–67 of FIG. 3 can be used in combination to set the maximum and minimum boundary conditions. Alternatively, one or more additional buttons can be included within the user interface of FIG. 3 to provide the adjustment mechanism.

Another embodiment of the invention internally resets the start/stop button 58 when the system senses the lack of spectral information for a preselected period of time. Thus, after the preselected period, the system has an automatic time-out, resulting in the microprocessor subsystem 12 resetting itself as if the start/stop button 58 were pushed.

Accelerometers are commercially available and are relatively cheap items. They are also small, so that all of the components 12, 14, 16 and 20 may easily fit within a small, lightweight housing. Suitable accelerometers include those accelerometers shown and described in connection with FIGS. 13, 14 and 14A.

Loft Sensor: Microphone Embodiment

A microphone, also well known to those skilled in the art, detects sound waves and provides a voltage output that is responsive to the detected sound waves. Accordingly, a microphone, like the accelerometer, senses the vibration of a vehicle, such as a ski or mountain bike, moving along a surface, e.g., a ski slope or mountain bike trail. By way of analogy, consider putting one's ear flat onto a desk and running an object across the desk. As one can readily determine, the movement of the object on the desk is readily heard in the ear. Likewise, a microphone as the loft sensor 20 readily "hears" the vibrational movements of the vehicle on the surface. Therefore, like the aforementioned accelerometer, a vibrational spectrum such as shown in FIG. 4 is generated by the microphone loft sensor during a user's sporting activity. As above, the microprocessor subsystem 12 utilizes the spectrum to determine "air" time.

Like accelerometers, microphones are also commercially available and are relatively cheap. They are also small, so that all of the components 12, 14, 16 and 20 may easily fit within a small, lightweight housing.

Figure 5:
FIG. 5 shows a microphone-based loft sensor constructed according to the invention and which is suitable for use in the system of FIG. 1.

FIG. 5 illustrates one embodiment of a microphone assembly 80 suitable for use with the invention. Specifically, a system 82 constructed according to the invention mounts, for example, to a ski 84 (for illustrative purposes, only the loft sensor portion 80 and microprocessor subsystem 81 are shown as part of the system 82 even though other components such as the display and user interface are present within the system 82). The microphone assembly 80 preferably includes a tube portion 86 to funnel the sound waves 88 coming from the ski surface 90 to the microphone element 92, e.g., a piezoelectric element known to those skilled in the art. During operation, the vibrational motion caused by the ski's interaction with the surface underneath the ski generates the sound waves 88 detected by the element 92, which converts the sound waves to voltages. These voltages are sampled and stored in the microprocessor subsystem 12 so that the information can be processed to extract the "air" information.

Depending on the sensitivity of the accelerometers and microphone assemblies, described above, it is feasible to attach the system of the invention directly to a user of the system as opposed to the vehicle. The vibrational or sound information is transmitted through the user to some degree while the user is on the ground, and such information can be used, as above, to calculate "air" time. Accordingly, one embodiment of the invention includes a system which measures "air" time that mounts directly to a user rather than to the vehicle, e.g., a ski.

Loft Sensor: Weight Switch Embodiment

In still another embodiment of the invention, the sensor 80 of FIG. 1 can be a switch that rests below the boot of the ski, e.g., the boot 30 of FIG. 2, and that senses pressure caused by the weight of the user within the boot. That is, when the skier is on the ground, the boot squeezes the switch, thereby closing the switch. The closed switch is detected by the microprocessor subsystem 12 (FIG. 1) as a discrete input. When a skier jumps into the air, the switch opens up by virtue of the fact that relatively no weight is on the switch; and this opened switch is also detected and input into microprocessor subsystem 12. The microprocessor subsystem 12 will count at known time intervals (clock rates) for the duration of the opened switch, corresponding to the jump, and will record how long the jump lasts.

As described in connection with FIG. 3, the "air" time may be recorded as a single jump, or recorded as a successive list of jumps. In addition, the "air" time can be summed or integrated into a running total, such as described above.

Figure 6:
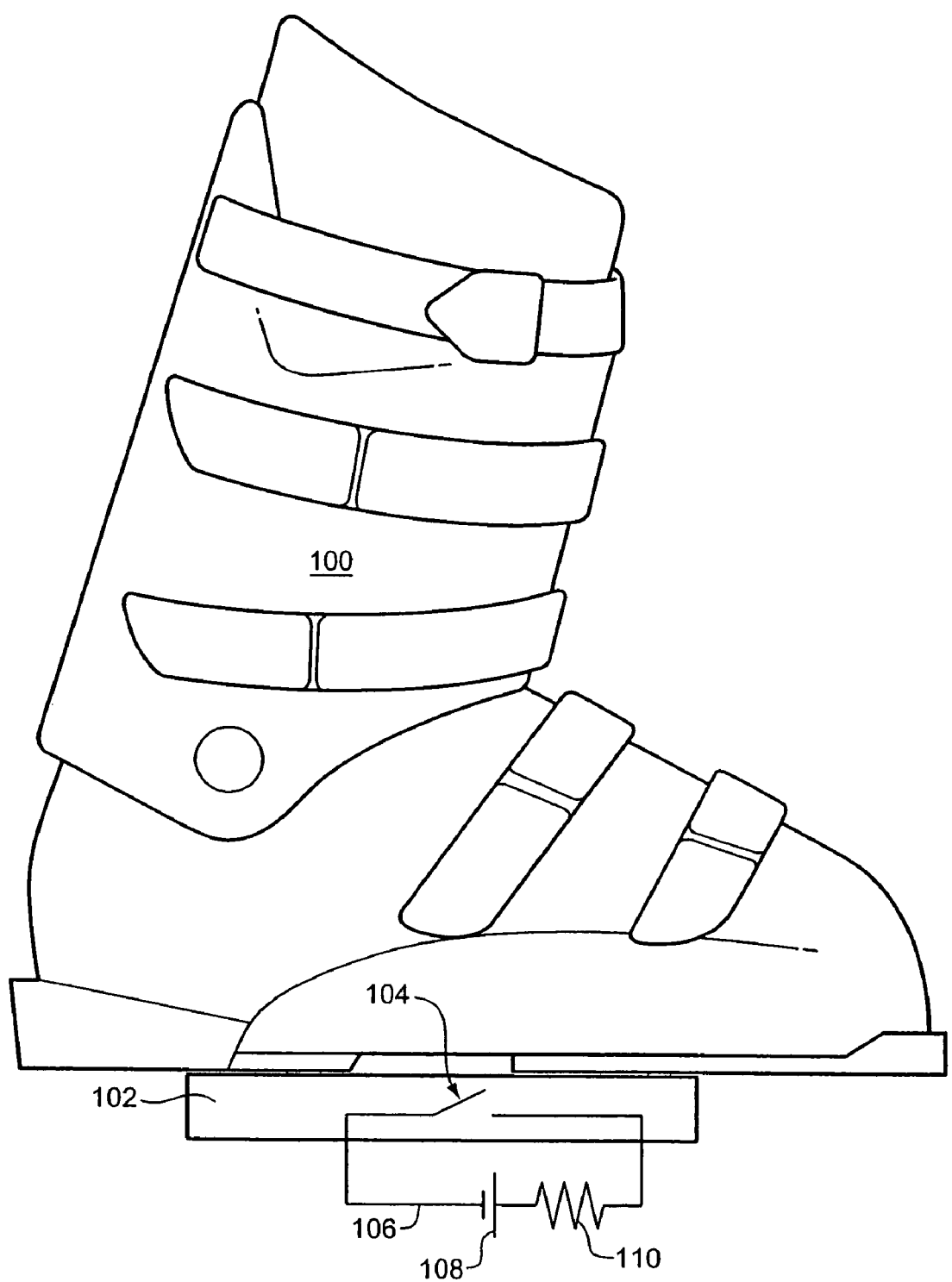
FIG. 6 shows a switch-based loft sensor constructed according to the invention and which is suitable for use in the system of FIG. 1.

FIG. 6 illustrates the manner in which one switch is formed, in accord with the invention (for illustrative purposes, the drawing of FIG. 6, like most of the drawings herein, are not to scale; and further shows disproportionate sizes of elements of the invention at least). A boot 100 (e.g., the ski boot 30 of FIG. 2) rests on top of a compressible material 102, e.g., foam, that includes a switch 104. When the user steps on the compressible material 102, the compressible material 102 compresses and causes the switch 104 to close, completing the circuit 106 (for illustrative purposes, the circuit 106 is shown simply as a switch 104, battery 108 and resistor 110; and the circuit 106 is shown externally when in fact the circuit is within the system of the invention and in communication with the microprocessor subsystem 12). When the switch 104 is closed, the circuit is in an ON condition, and when the switch 104 is not closed, the system is in an OFF condition. Accordingly, the microprocessor subsystem 12 senses the ON and OFF conditions to calculate "air" time. Specifically, the time between an OFF condition and an ON condition can be used to determine "air" time.

Figure 7:
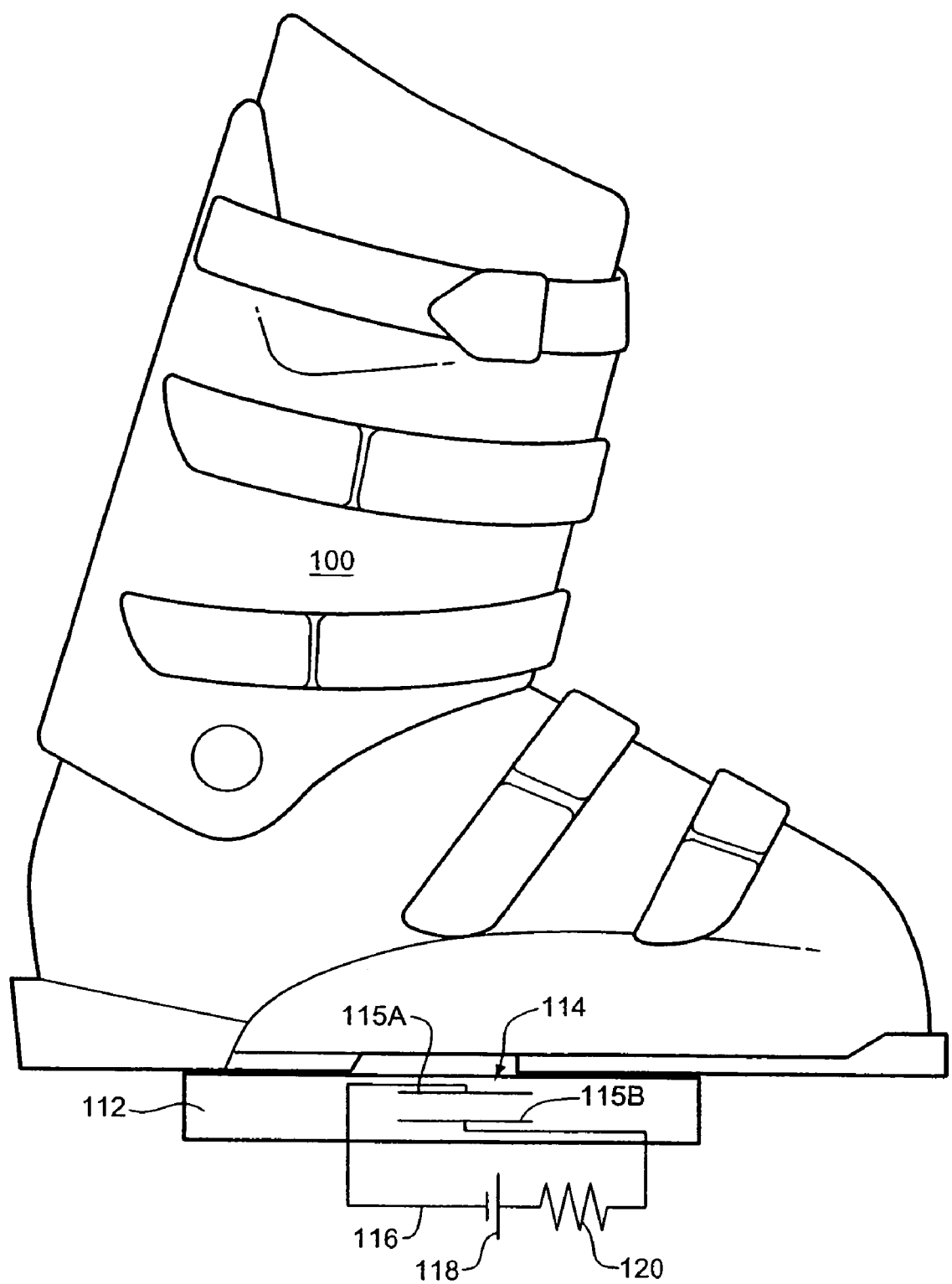
FIG. 7 shows a capacitance-based loft sensor constructed according to the invention and which is suitable for use in the system of FIG. 1.

Another embodiment of the invention which is suitable for use as the loft sensor 20, FIG. 1, includes a pad that is placed under the skier's boot and that changes capacitance as a function of a change of applied pressure. For example, consider FIG. 7 (again with illustrative ski boot 100) which shows a compressible material 112 and a capacitance-changing element 114 that changes capacitance under varying applied pressures. This capacitance-changing element 112 is connected in circuit 116, including the illustrative battery element 118 and resistor 120, with the system of the invention such that its capacitance is converted to a digital signal by conditioning electronics, such as shown in FIG. 8. As above, the circuit of FIG. 7 is shown illustratively and without the other necessary components (e.g., the microprocessor subsystem) of the invention. Those skilled in the art understand that the components 112, 114, 115, 116, 118 and 120 connect integrally with a system (e.g., the system 10 of FIG. 1) constructed according to the invention.

By way of background, a capacitor consists of two parallel plates separated by a dielectric material. The capacitance is directly proportional to the cross sectional area of the plates and inversely proportional to the distance between the plates. When the dielectric is the compressible material 112, FIG. 7, then the pressure applied to the material 112 changes the distance between the plates 115a, 115b of the capacitance-changing element 114, thereby proportionately increasing the capacitance.

FIG. 8 shows a monostable multivibrator 122, e.g., a NE555, in accord with the invention which converts the varying capacitance (illustrated as portion 124) from the capacitance-changing element 114 of FIG. 7 to information suitable for calculating "air" time. A resistor 126 connects in circuit with the portion 124 and the multivibrator 122. The output pulse train 128 is directly dependent on the product of the resistance "R" and variable capacitance "C". The resistance R may be fixed while the capacitance C is dependent on the pressure exerted on the pad 112 thus shifting the frequency of a pulse train 128. The pulse train 128 repetition rate is indicative of the value of capacitance of 124. When the pulse train 128 repetition rate increases the value of C 124 has decreased and the skier's boot is applying less pressure on the pad 112. This event marks the beginning of the "air time" measurement. When the pulse train 128 repetition rate decreases, meaning a sudden increase of capacitance, the boot is now applying greater pressure on the ski, signifying the end of the "air" time measurement. The length of time that the pulse train 128 remains at the higher repetition rate is equal to the amount of time the ski is off the ground. That amount of time is the loft or "air" time.

Alternatively, and such as shown in FIG. 9, the change in capacitance can be used in a filter which passes a pulse train during low capacitance levels (no boot pressure) and which filters out the pulse train during high capacitance events (high boot pressure). For example, a capacitance-changing element 130 (e.g., the capacitance-changing circuit 116 of FIG. 7) connects to the input of a Schmidtt Trigger CMOS gate 133 and ground. A pulse generator 131 connects through a fixed resistor R132 to the capacitance-changing element 133 and the Schmidtt Trigger CMOS gate 133. The pulse generator 131 produces a steady pulse train 134. When the capacitance changing element 130 is at a high capacitance, corresponding to a high boot pressure meaning that the ski is on the ground, the combination of the fixed resistance R 132 and the capacitance of the capacitance-changing element 130 absorbs the pulse train and the output of the Schmidtt Trigger CMOS gate 133 is constant. On the other hand, when the skier takes flight, the capacitance of the capacitance-changing element 130 is low, thus allowing the pulse train 134 to pass through to the Schmidtt Trigger CMOS gate 133 input. The output of the Schmidtt Trigger CMOS gate 133 in this latter case toggles at the same rate as the pulse train 131, thereby identifying a condition of "air" time. A discrete input is thus used by the processor to sample for the existence of the pulse train to calculate "air" time.

Microprocessor Subsystem

The microprocessor subsystem 10 of FIG. 1 can include a microcontroller element, a Microcontroller element with reduced functionality to conserve power, or a microprocessor element with associated memory and logic to perform the requisite calculations of the invention, including the processing power to drive the display 16 and user interface 14.

Figure 10:
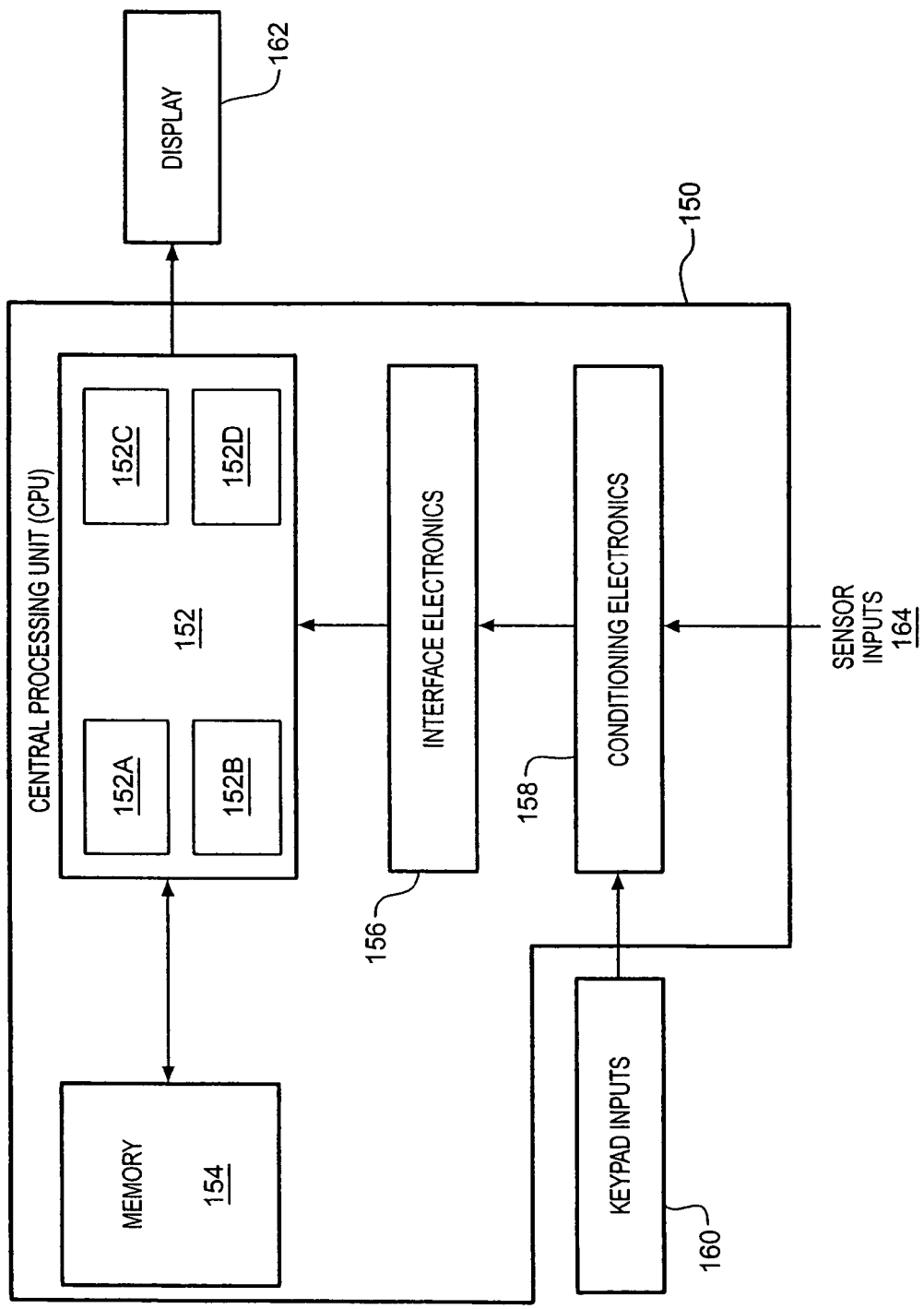
FIG. 10 schematically illustrates a microprocessor subsystem constructed according to the invention and which is suitable for use in the system of FIG. 1.

Preferably, however, the microprocessor subsystem 12 is constructed by several known components, such as shown in FIG. 10. FIG. 10 shows microprocessor subsystem 150 constructed according to the invention and including a Central Processing Unit (CPU) 152, memory 154, interface electronics 156, and conditioning electronics 158. The user interface 160, such as the interface 14 of FIG. 1, and including the button inputs of FIG. 3, connects to the subsystem such as shown and directly to the conditioning electronics 158. The display 162, such as the display 16 of FIG. 1, preferably connects to the subsystem such as shown and directly to the CPU 152.

The CPU 152 includes a microprocessor 152a, Read Only Memory (ROM) 152b (used to store instructions that the processor may fetch in executing its program), Random Access Memory (RAM) 152c (used by the processor to store temporary information such as return addresses for subroutines and variables and constant values defined in a processor program), and a master dock 152d. The microprocessor 152a is controlled by the master clock 152d that provides a master timing signal used to sequence the microprocessor 152a through its internal states in its execution of each processed instruction. The dock 152d is the master time source through which time may be deduced in measuring velocity or air time (for example, to determine the elapsed time from one event to another, such as the lapsed time "t1" to "t2" of FIG. 4, the clock rate provides a direct measure of time lapse).

The microprocessor subsystem 150, and especially the CPU 152, are preferably low power devices, such as CMOS; as is the necessary logic used to implement the processor design.

The subsystem 150 stores information about the user's activity in memory. This memory may be external to the CPU 152, such as shown as memory 154, but preferably resides in the RAM 152c. The memory may be nonvolatile such as battery backed RAM or Electrically Erasable Programmable Read Only Memory (EEPROM). External signals 164 from the speed and/or loft sensors, e.g., the speed sensor 18 and loft sensor 20 of FIG. 1, are connected to the conditioning electronics 158 which filters, scales, and, in some cases, senses the presence of certain conditions, such as zero crossings. This conditioning essentially cleans the signal up for processing by the CPU 152 and in some cases preprocesses the information. These signals are then passed to the interface electronics 156, which converts the analog voltage or currents to binary ones and zeroes understood by the CPU 152.

The invention also provides for intelligence in the signal processing, such as achieved by the CPU 152 in evaluating historical data. For example, "air" time may be determined by the noise spectra that changes abruptly, such as indicating a leap, instead of a noise spectra representing a more gradual change that would occur for example when a skier slows to a stop. As previously noted, a minimum quiet time is required, in certain embodiments of the invention, to differentiate between "air" time and the natural motions associated with turning and skiing (e.g., jump skiing). Further, in other certain embodiments, a maximum time is also programmed to differentiate "air" time from an abrupt stop, such as standing in a lift line.

Speed Sensor

In accord with the invention, if speed is calculated within the system, the speed sensor 118 of FIG. 1 can take one of several forms, including: (1) a pitch detection system that detects the "pitch" of the vibrational spectrum and that converts the pitch to an equivalent speed; (2) a laser-based or sound-based Doppler-shift sensor; (3) an accelerometer-based speed sensor; (4) a pressure-based speed sensor; and (5) a voltage-resistance sensor It should be noted that in either of the speed or loft sensors, it may be preferable to incorporate state machine logic within the sensor in order to pre-process the data for the microprocessor subsystem. Thus, in accord with the invention, processing logic such as described herein in connection with the microprocessor subsystem can be incorporated, at least in part, within one or both of the speed and loft sensors. Because of the complexity of the speed sensor, such preprocessing power is more appropriately within the speed sensor.

Speed Sensor: Pitch Detection

In accord with this embodiment, no separate speed sensor element, e.g., the sensor 18 of FIG. 1, is required. Rather, the vibrational spectrum that is generated by the loft sensor 20, and particularly the accelerometer or microphone embodiment discussed in connection with FIG. 4, will be used to determine the pitch of the vibration and, thereby, the equivalent speed. By way of example, note that a skier generates a scraping sound on hard-packed snow and ice. When the skier changes velocity, that scraping sound changes in pitch. The spectrum shown in FIG. 4 outside the t1/t2 region (but within the "start" and "end" region) is, effectively, that pitch. By calibrating the microprocessor subsystem 12 to associate one pitch as one velocity, and so on, the speed of the vehicle (e.g., ski and mountain bike) may be determined by spectral content.

In accord with the invention, one method for determining the "pitch" of the spectrum outside the t1/t2 loft region of FIG. 4 (and within the start/stop time) is to determine the "best fit" sine wave to the vibrational spectrum data. This sine wave will have a frequency, or "pitch" that may be quantified and used to correlate velocity.

This spectral content may be determined, in part, by the conditioning electronics 158 of FIG. 10 such to determining rise times to infer a bandwidth of the information. The conditioning electronics 158 and/or CPU 152 can also measure the time between successive zero crossings, which also determines spectral content.

Figure 11:
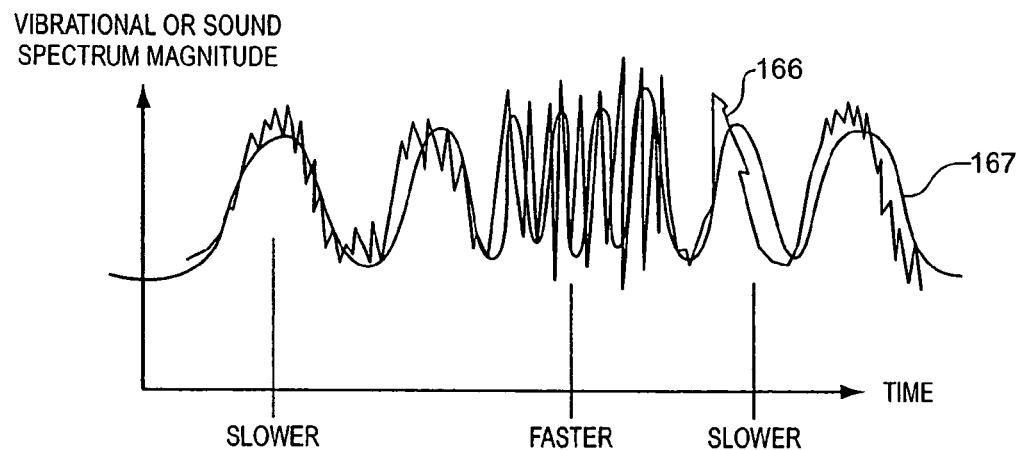
FIG. 11 illustrates one exemplary pitch-detection process, in accordance with the invention, which is used to determine the speed of a vehicle.
Figure 13:
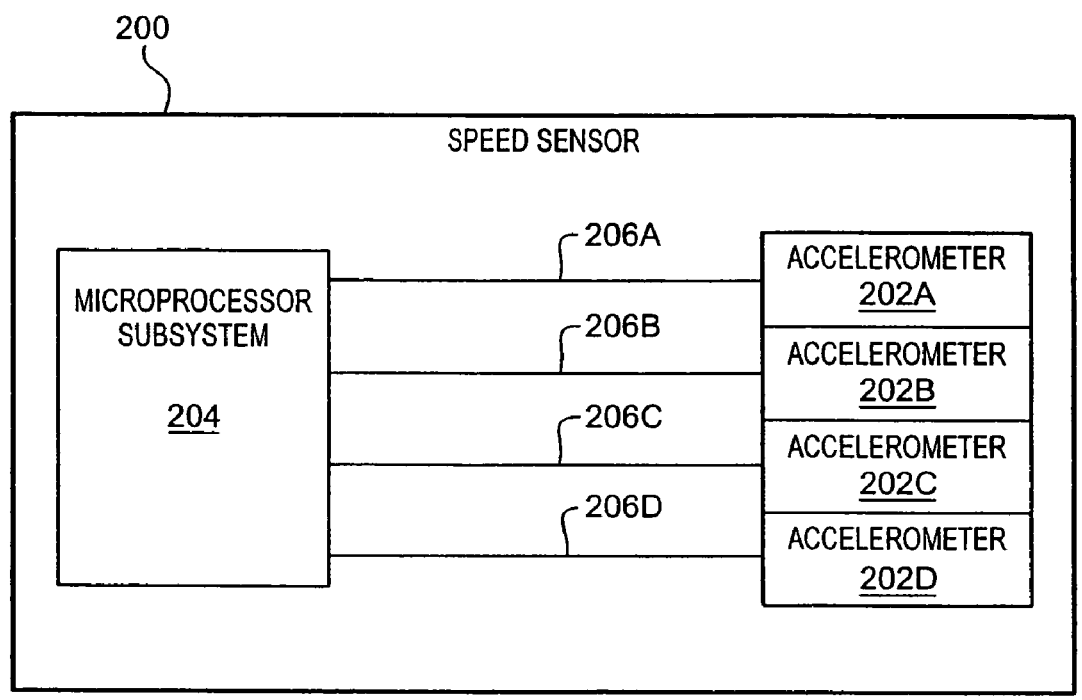
FIG. 13 illustrates an accelerometer-based speed sensor constructed according to the invention and which is suitable for use as both the speed and loft sensors of FIG. 1.

For example, FIG. 11 illustrates a spectrum 166 generated from a sensor such as a sensor 18 or 20 (FIG. 1), or 82 (FIG. 5), or 202a–202d (FIG. 13 below). The spectrum 166 thus represents an acceleration spectrum or sound spectrum such as described herein. The microprocessor subsystem 12 of FIG. 1 evaluates the spectrum 166 and generates a best-fit sine wave 167 to match the primary frequency of the spectrum 166 over time. FIG. 11 shows illustratively a situation where a vehicle, such as a ski, moves slowly at first, corresponding to a lower sine-wave frequency, then faster, corresponding to a higher frequency sine wave, and then slower again. This pitch transition is interpreted by the microprocessor subsystem (e.g., the subsystem 12 of FIG. 1) as a change of speed. Specifically, the microprocessor subsystem of the invention is calibrated in this embodiment to associate a certain frequency with a certain speed; and speed is thus known for the variety of pitches observed during an activity, such as illustrated in FIG. 11.

It should be noted that the pitch information is surface dependent (and vehicle dependent). That is, a ski-over-snow-speed-spectrum has a different spectrum than a bicycle-over-ground-spectrum. Accordingly, different calibrations must be made for different vehicles and speeds, in accord with the invention. Further, certain spectrums may actually decrease in frequency as speed increases; which also must be calibrated to obtain the correct speed information. These calibrations are typically programmed into the microprocessor subsystem memory, e.g., the memory 13 of subsystem 12 of FIG. 1. Further, in certain embodiments of the invention, the system stores different spectrum calibrations for different activities so that a user can move the system from one sport to another. Accordingly, one or more buttons such as the buttons 58–67 of FIG. 3 are introduced to the user interface, such as known to those skilled in the art, in order to selectively access the different spectrum calibrations.

Speed Sensor: Doppler-based

It is well known that Doppler radar is used by police vehicles to detect speed. In accord with this embodiment of the invention, the same principles apply to the measurement of speed of the sporting vehicle. For example, consider FIG. 12.

Figure 12:
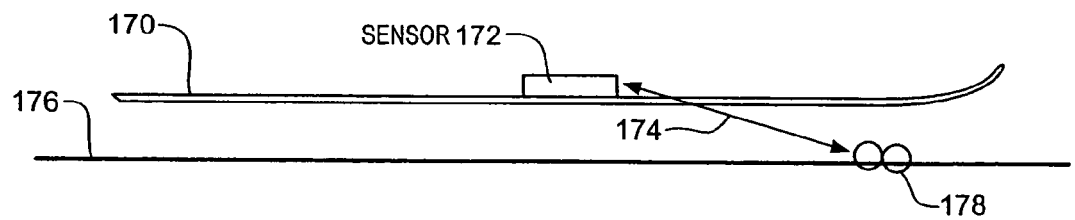
FIG. 12 illustrates a Doppler-based approach to sensing speed in accordance with the invention.

FIG. 12 shows a representative ski 170 (partially shown) with a Doppler-based sensor 172 mounted thereon (for illustrative purposes, the Doppler-based sensor is shown without the other elements of the system, such as the user interface and microprocessor). The sensor generates an electromagnetic beam 174, such as a laser beam, to bounce off the ground 176 (e.g., the ski slope) while the user of the system conducts the activity (e.g., skiing). The electromagnetic beam 174 is reflected off the ground by particles 178 which scatter at least a portion of the energy back to the sensor 172 along approximately the same path. Because the ski 170 is in motion, the returned energy is at a slightly different frequency from the outgoing frequency; hence the Doppler shift, which is a measurable quantity. Note that the sensor 172 must be arranged to generate a beam along the side (or in front or back of) the ski in order to "see" the ground 176.

Figure 12A:
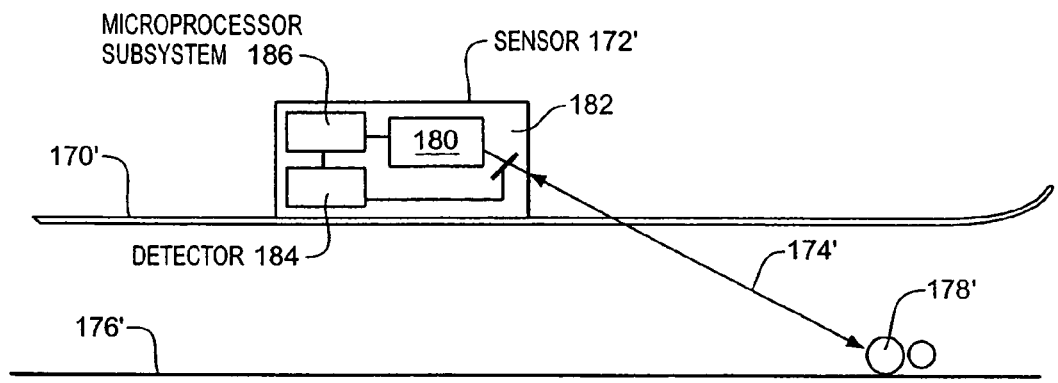
FIG. 12A shows a laser-based Doppler speed sensor constructed according to the invention.

The energy beam 174 is generated in one of two general ways: by a laser diode (to generate a laser beam) or by a piezoelectric transducer (to produce an ultrasonic beam). FIG. 12a, for example, shows a sensor 172' comprising a laser diode 180. The diode 180 generates a laser beam 174' which is reflected by the particles 178' back to the sensor 172'. A small beam-splitting mirror 182 reflects part of the returned beam to a detector 184 which is connected under the overall control of the microprocessor subsystem 186, e.g., the subsystem 12 of FIG. 1 (for illustrative purposes, the other elements of the system of the invention, e.g., the user interface, are not shown in FIG. 12a). The subsystem 186 evaluates the frequency difference between the outgoing beam from the diode 180 and the returned frequency from the detector 184. The frequency difference is readily converted to speed that is displayed on the display, e.g., the display 16 of FIG. 1.

Figure 12B:
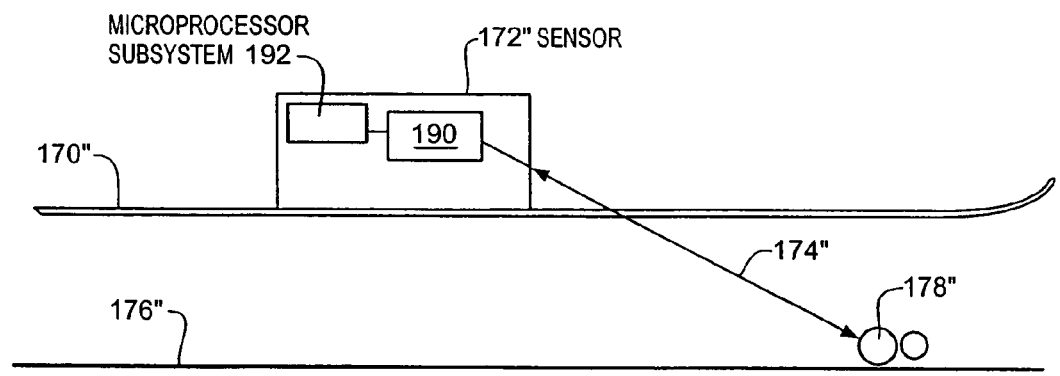
FIG. 12B shows an ultrasonic-based Doppler speed sensor constructed according to the invention.

Likewise, FIG. 12b shows a sensor 172" comprising a piezoelectric transducer 190 which generates an ultrasonic beam 174" that reflects from particles 178" back to the piezo transducer 190, which is connected under the overall control of the microprocessor subsystem 192, e.g., the subsystem 12 of FIG. 1 (for illustrative purposes, the other elements of the system of the invention, e.g., the user interface, are not shown in FIG. 11b). The microprocessor subsystem 192 generates a voltage at a set frequency to drive the piezoelectric transducer 190, to thereby generate the beam 174". The reflected Doppler-shifted beam returns through the transducer 190 (alternatively, through another piezo transducer (not shown)) and generates a voltage at the frequency of the reflected beam. The subsystem 192 evaluates the frequency difference between the outgoing ultrasonic beam 174" and the returned frequency. As above, the frequency difference is readily converted to speed (via a conversion technique that is known to those skilled in the art) that is displayed on the display, e.g., the display 16 of FIG. 1.

Figure 27:
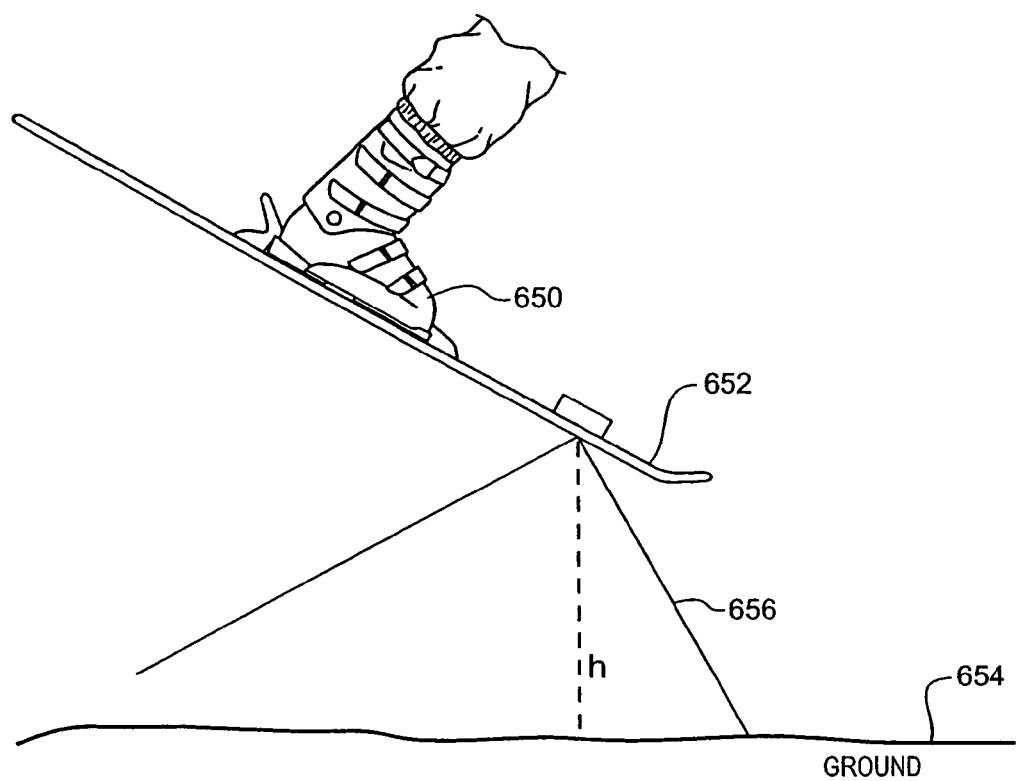
FIG. 27 shows a technique for measuring height, in accord with the invention, such as for a skier's height.

A Doppler system such as described can additionally provide height information. That is, by sweeping the frequency through various frequencies, the signal frequency mix can be monitored to determine altitude relative to the direction of the antenna lobes. Preferably, therefore, there are two antennas: one to perform Doppler speed, with high spatial accuracy in the antenna lobe so that speed is achieved, and another antenna to provide a love that roughly covers the ground area in about a 60 degree cone under the user so as to achieve first-return distance measurement. That is, with reference to FIG. 27, a doppler system 648 placed relative to a skier 650 on a ski 652 should adequately cover the ground 654 so as to provide the correct measure of height "h." A cone 656 of adequate angle Ô (e.g., 25–70 degrees in solid angle) provides such a coverage. The Doppler antenna signal love fills the cone 656 so as to determine first return height "h" from the correct orientation of the ski 652.

Loft Sensor: Accelerometer Based

Modern navigation systems utilize a plurality of accelerometers to determine speed and direction. Particularly complex military systems, for example, utilize three translational and three rotational accelerometers to track direction and speed even during complex angular movements and at extremely high velocities.

In accord with the invention, a similar plurality of accelerometers is used to determine speed. However, unlike military systems, one goal of the invention is to track speeds of sporting vehicles (eg., a ski) that generally travel in one direction, namely forward. Therefore, the complexity of the accelerometer package is reduced since the orientation of the sensor may be fixed to the vehicle; and fewer than six accelerometers can be used to determine speed.

Accelerometers are well-known to those skilled in the art. They include, for example, translational and rotational accelerometers. FIG. 13 illustrates a speed sensor 200 constructed according to the invention and which includes a plurality of accelerometers 202a–202d. The accelerometers 202a–202d sense various accelerations in their respective axes (accelerometers sense acceleration along a predefined axis, translational or rotational), and each of the outputs from the accelerometers are input to the microprocessor subsystem 204, e.g., the subsystem 12 of FIG. 1, via communication lines 206a–206d. The orientation of the sensitive axis of each accelerometer 202a–202d is stored in the microprocessor subsystem 204 so that a particular acceleration in one axis is properly combined with acceleration values in other axes (as described in more detail below in connection with FIGS. 14 and 14a).

One key point that must be addressed with the accelerometer-based approach: gravity has a huge effect on the accelerometer signals; and gravity must be compensated for in order to achieve reasonable speed accuracy. Therefore, one or more of the accelerometers 202a–202d are used to determine and measure the force or gravity relative to the angle of the vehicle (e.g., the ski) so that gravity may be compensated for by the subsystem 204. Specifically, when the sensor 200 is pointed either downhill or uphill, gravity tends to reduce or increase the measured acceleration output; and that reduction or increase must be adjusted for or else the conversion from acceleration to speed (i.e., the integral of acceleration over time) will be next to useless. Accordingly, the orientations of the accelerometers 202a–202d relative to their respective sensitive axes must be known by the subsystem 204 in order to compensate for the acceleration of gravity, which is generally perpendicular to the motion of the vehicle, but which has a component acceleration in the direction of movement when the vehicle is pointed downwards or upwards.

It should be clear to those skilled in the art that fewer, or greater, numbers of accelerometers are within the scope of the invention, so long as they collectively determine speed. In effect, the fewer number of accelerometers results in reduced accuracy; not reduced functionality. Rather, in an ideal situation, one accelerometer can be used to detect speed; which is the integral of the acceleration over time. Further, a double integration over the same period provides distance; and, therefore, the invention can also provide distance in at least one embodiment of the invention.

It should also be noted that any of the accelerometers 202a–202d of FIG. 13 can be used, in accord with the invention, as the loft sensor 20 of FIG. 1 and without a separate component to measure "air" time. This is because each of the accelerometers 202a–202d generate a spectrum such as described in connection with FIG. 4. Accordingly, one or more of the accelerometers 202a–202d can be used to determine "air" time, described above, without the need for a separate loft sensor.

Figure 14:
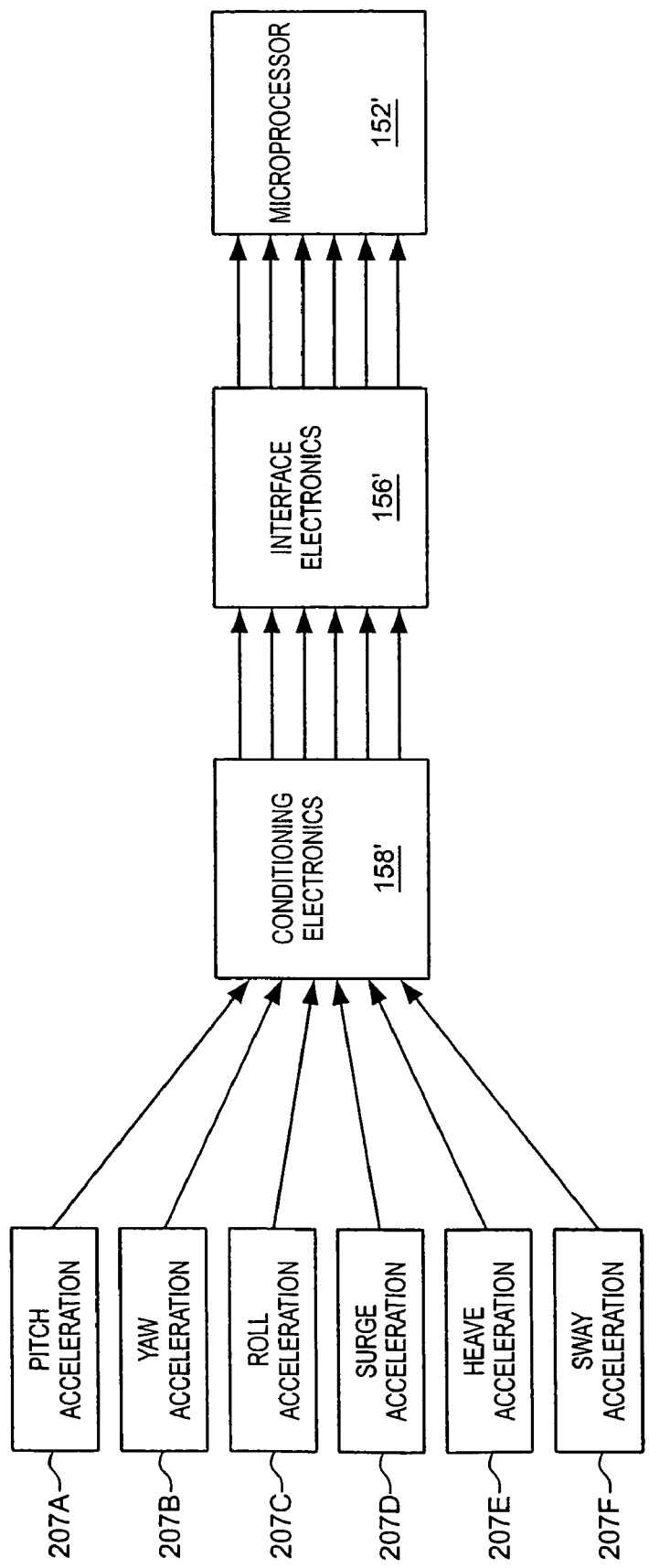
FIG. 14 schematically illustrates process methodology of converting a plurality of acceleration values to speed, in accord with the invention.

FIG. 14 schematically illustrates process methodology, according to the invention, which converts a plurality of acceleration inputs to speed. For example, when a plurality of six accelerometers (e.g., similar to the accelerometers 202a–202d of FIG. 13) are connected to a microprocessor subsystem such as the subsystem 150 of FIG. 10, the process methodology of the invention is preferably shown in FIG. 14. Specifically, six accelerometers are connected with various sensitive orientations to collect pitch 207a, yaw 207b, roll 207c, surge 207d, heave 207e, and sway 207f accelerations. These accelerations are conditioned by the conditioning electronics 158' through the interface electronics 156' and CPU 152' to calculate speed, such as known to those skilled in the art of navigational engineering (for example, *Gyroscopic Theory Design, and Instrumentation* by Wrigley et al., MIT Press (1969); *Handbook of Measurement and Control* by Herceg et al, Schaevitz Engineering, Pensauker, N.J., Library of Congress 76-24971 (1976); and *Inertial Navigation Systems* by Broxmeyer, McGraw-Hill (1964) describe such calculations and are hereby incorporated herein by reference). The elements 158, 156' and 152' are similar in construction to the elements 158, 156 and 152 described in connection with FIG. 10.

Figure 14A:
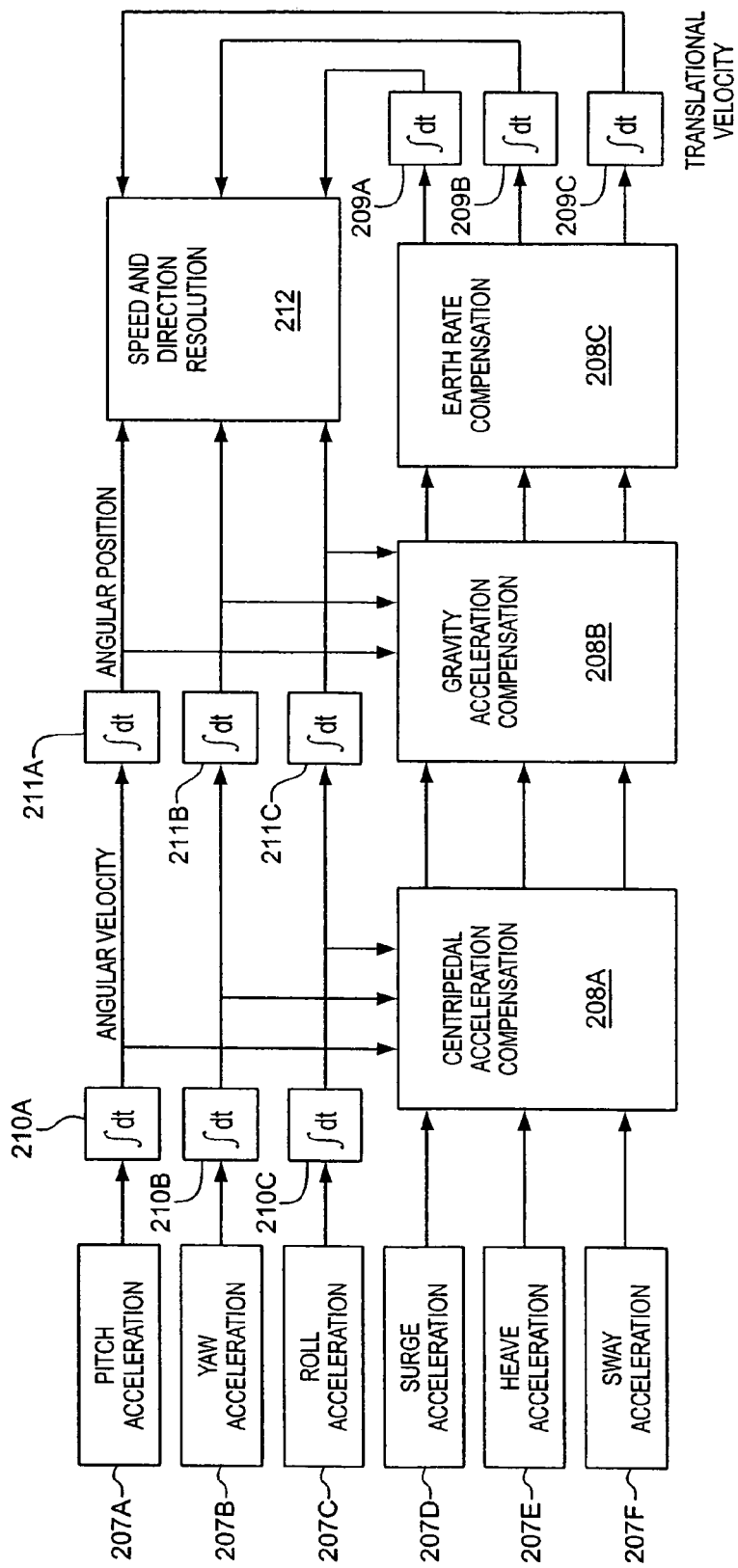
FIG. 14A schematically illustrates a process methodology of calculating speed, direction, and vehicle height, in accord with the invention, by utilizing the accelerometer-based sensors of the invention.

FIG. 14A schematically illustrates further process methodologies according to the invention wherein the six acceleration inputs 207a–207f are processed by the microprocessor subsystem of the invention (e.g., subsystem 12 of FIG. 1) such that centripetal, gravitational, and earth rate compensations are performed so that the various accelerations are properly integrated and compensated to derive speed (and even direction and distance). Specifically, a microprocessor subsystem of the FIG. 14A embodiment includes a centripetal acceleration compensation section 208a which compensates for motions of centripetal accelerations via inputs of surge 207d, heave 207e, and sway 207f. A gravity acceleration compensation section 208b in the subsystem further processes these inputs 207d–207f to compensate for the acceleration of gravity, while a earth rate compensation section 208c thereafter compensates for the accelerations induced by the earth's rotation (e.g., the earth rate acceleration at the equator is approximately opposite in direction to the force of gravity).

Also shown in FIG. 14A are translational integrators 209a–209c which convert the compensated accelerations from inputs 207d–207f to translational velocities by integration. Integrators 210a–210c likewise integrate inputs of pitch 207a, yaw 207b, and roll 207c to angular velocity while integrators 211a–211c provide a further integration to convert the angular velocities to angular position. The angular positional information and translational velocity information is combined and processed at the speed and direction resolution section 212 to derive speed and direction. Preferably, the subsystem with the components 208, 209, 210, 211 and 212 is calibrated prior to use; and such calibration includes a calibration to true North (for a calibration of earth rate).

It should be noted that fewer of the inputs 207a14 207f may be used in accord with the invention. For example, certain of the inputs 207a–207f can be removed with the section 208a so that centripetal acceleration is not compensated for. This results in an error in the calculated speed and direction; but this error is probably small so the reduced functionality is worth the space saved by the removed elements. However, with the increased functionality of the several inputs 207a–207f, it is possible to calculate loft height in addition to speed because distance in three axes is known. Therefore, the invention further provides, in one embodiment, information for displaying height achieved during any given "air" time, as described above.

The system of FIG. 14A can additionally measure skier height, off of the ground, through integration of appropriate acceleration vectors indicative of a user's movement perpendicular to the ground. Snowboarders, skiers and windsurfers (and others) have a desire to know such quantities. A double integration of accelerometers in the direction perpendicular to ground (or thereabouts) during a "loft" time measurement provides the correct signals to determine skier height.

It should be apparent to those in the art that the accelerometers of FIGS. 13–14 provide sufficiently detailed information such that the whole of the system according to the invention can be mounted to a user of the system directly, rather than directly to a vehicle. With the scope of the compensations described in connection with FIG. 14A, for example, movements of the human body, e.g., centripetal motions, may be compensated for to derive speed and/or loft time information that is uncorrupted by the user's movements. Such compensations, however, require powerful processing power.

Speed Sensor: Pressure Based

Figure 15:
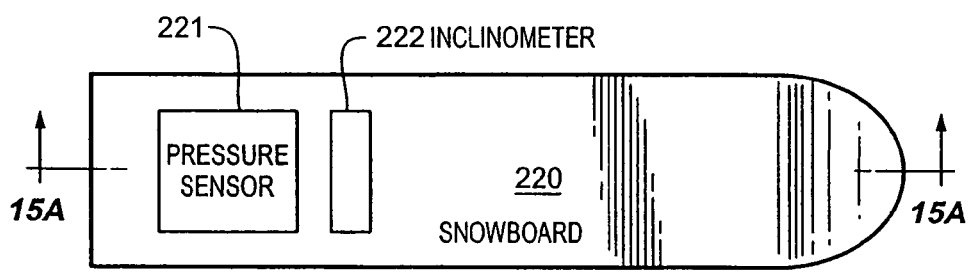
FIGS. 15 and 15A illustrate a pressure-based speed sensor constructed according to the invention.
Figure 15A:
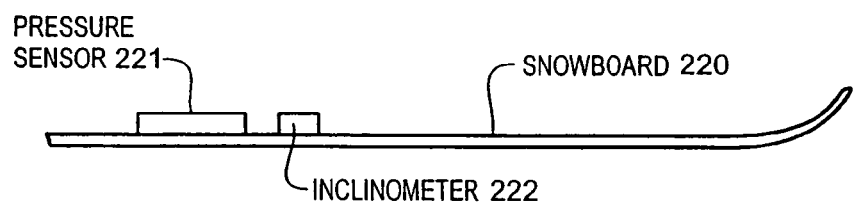

Pressure of the air is used in aviation to determine how high an aircraft is the higher the altitude the lower the air pressure. Pressure sensors according to the invention convert air pressure to an analog voltage. When mounted to a snowboard 220, such as shown in FIGS. 15 and 15A, the pressure sensor 221 is used to determine the altitude of the snowboarder. This voltage is read by the microprocessor subsystem (e.g., the subsystem 12 of FIG. 1) at a fixed rate and differentiated to determine rate of descent or speed in the vertical direction. This may be converted to speed along the path by knowing the grade or angle of descent. Angle of descent is known by predetermining the geometry of the ski path or by the addition of a inclinometer 222 which gives a voltage dependent upon the angle, with respect to vertical, of the platform. The inclinometer 222 measures zero when the ski is traveling along a level path and the pressure sensor is showing a constant pressure. When the ski moves downhill, for example, the inclinometer 222 measures the angle of descent and the pressure sensor measures ever increasing pressure. Since the angle of descent is known, as is the rate of descent, the true speed is determined and displayed.

Those skilled in the art should understand that the elements 221 and 222 are connected in circuit with the further elements of the invention, e.g., the microprocessor subsystem 12 of FIG. 1; and that elements 221 and 222 are shown in FIG. 15 for illustrative purposes only when in fact they exist integrally with the system of the invention, e.g., the system 10 of FIG. 1.

Speed Sensor: Voltage-Resistance Based

Figure 16:
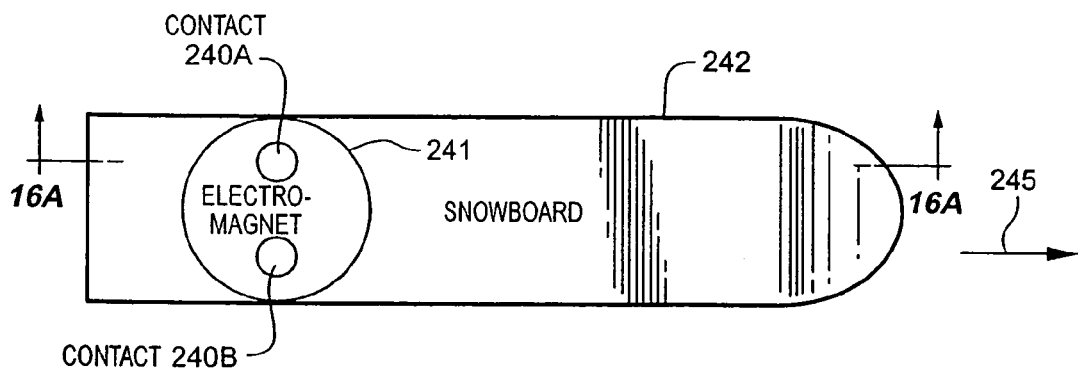
FIGS. 16 and 16A illustrate a magnetic/voltage-based speed sensor constructed according to the invention.
Figure 16A:
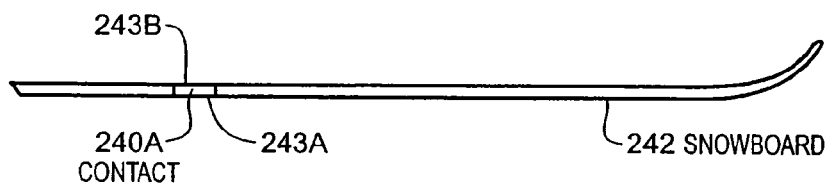

Under-water vehicles and many oceanographic instruments measure water velocity by taking advantage of the principle discovered by Faraday that a conductor moving through a magnetic field produces a voltage across the conductor. The voltage produced is greatest when the conductor is orthogonal to the magnetic field and orthogonal to the direction of motion. This principal is used, in accord with the invention, to determine the speed that a skier moves over the snow in winter skiing or over the water in water skiing. As shown in FIGS. 16 and 16A, an electromagnet 241 is mounted to a snowboard 242. Two contacts 240a, 240b are mounted to the snowboard 242 such that the bottom 243a makes contact with the snow and the top 243b of the contacts are connected to a voltage-measuring circuit within the conditioning electronics (such as the electronics 158 of FIG. 10 and such as known to those skilled in the art). When the snowboard 242 is flat on the snow, a conduction path is set up between the two contacts 240a, 240b and through the snow. When the electromagnet 241 is energized, a magnetic field 244 is imposed on the conduction path. As the snowboard 242 moves in the forward direction 245, the conduction path through the snow moves with the snowboard 242. This represents a moving conductor in a magnetic field; and as Faraday's theorem requires, a voltage 246 across the two terminals 240a, 240b will be generated that is proportional to the snowboarder's speed. This voltage 246 is read by the microprocessor subsystem (e.g., the subsystem 12 of FIG. 1). When the voltage abruptly goes to zero, and thereafter returns to a high voltage, the microprocessor subsystem determines that the gap in voltage is "air" time. Accordingly, in such an embodiment, no separate sensor 20 is required to measure "air" time (such as described above).

Figure 16B:
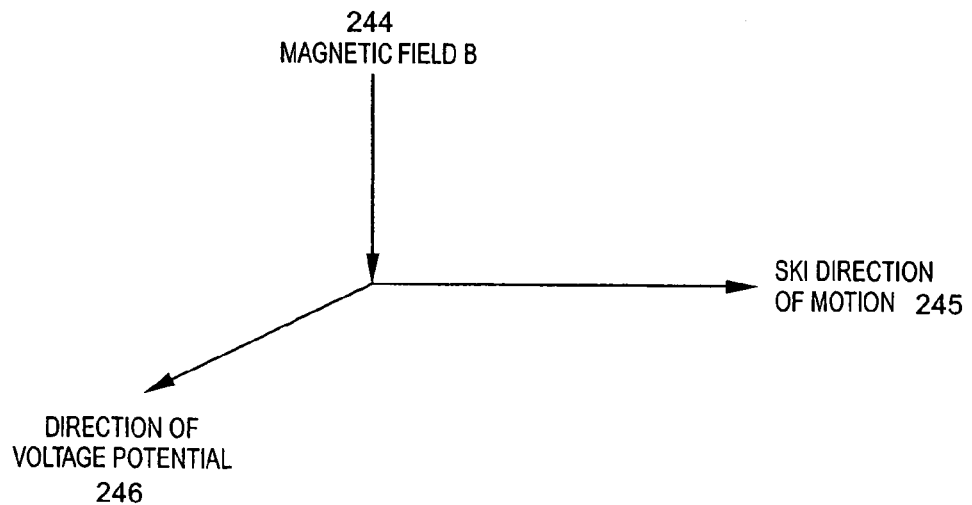
FIG. 16B shows relative motions, magnetic field directions, and voltages associated with the sensor of FIGS. 16 and 16A.

Those skilled in the art will appreciate that the elements of FIGS. 16–16B are shown illustratively for ease of understanding and without the further necessary elements of the invention, e.g., the microprocessor subsystem 12 of FIG. 1.

Figure 17:
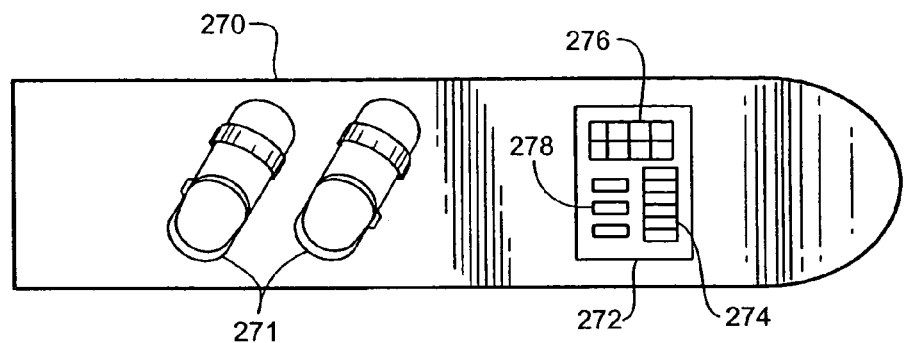
FIG. 17 illustrates an improvement to a snowboard in accord with the invention.

It should be clear to those skilled in the art that certain modifications can be made to the invention as described without departing from the scope of the invention. For example, vehicles other than skis and mountain bikes may be used with the invention. One vehicle, the snowboard, used in the ever popular snowboarding sport, is particularly well-suited for the invention (e.g., there is no jump skiing). The snowboard also has a wide body and a system constructed according to the invention can be incorporated within the body with the user interface, display, and associated buttons at the snowboard surface, for easy access. FIG. 17 shows such an improvement to a snowboard in accord with the invention. Specifically, a snowboard 270, with boot holder 271, incorporates a system 272 constructed according to the invention. The system 272, like the system 10 of FIG. 1, has a display 274, a user interface 276 that provides a user with buttons to selectively access speed and loft time, as described above, and one or more display portions 278 to display identification information about the displayed times (such as described in connection with FIG. 3).

Figure 18:
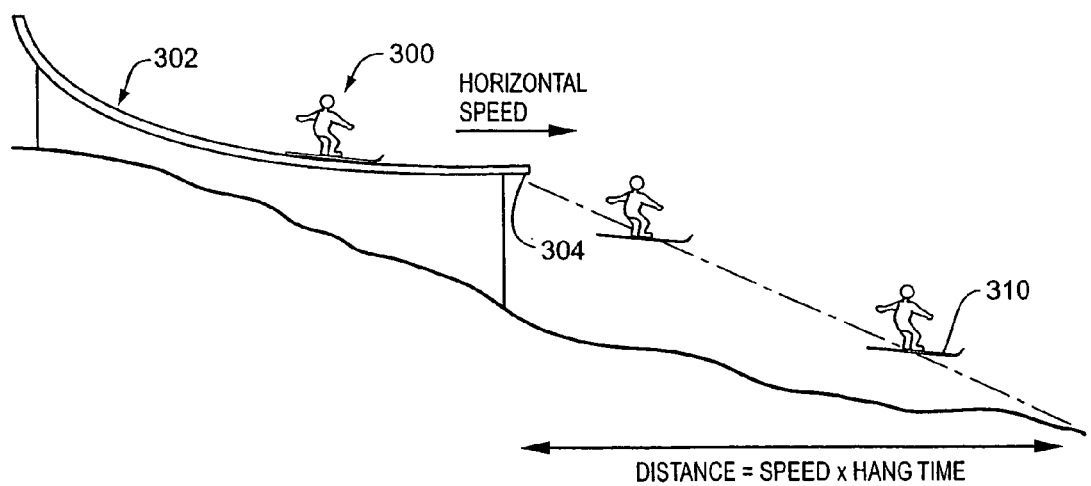
FIG. 18 illustrates one use of the invention for detecting speed, "air," and distance in the sport of ski flying (or ski jumping) in accord with the invention.

FIG. 18 shows yet another use of the invention. Specifically, a further application of the invention is found in the sport of ski jumping and ski flying. Ski flying is similar to ski jumping except that ski jumping uses special, extra-long skis, while ski flying uses standard alpine skis. The participant 300 skis down the long ramp 302, which may be as high as twenty-five stories, and launches horizontally into the air at the end 304 of the ramp 302. The objective of the sport is for the participant 300 to "jump" or "fly" through the air for as long as possible, and covering the greatest distance as possible. A system constructed according to the invention (not shown) is attached to the ski 310 to measure "air" time, speed, and distance, as described herein. In particular, the speed at the end 304 is used to predict distance by well-known Newtonian physics so that the participant's overall jump distance is calculated. This removes the necessity of having judges and/or other expensive equipment monitor the event, as the recorded "air" and jump distance is readily displayed by the system of the invention.

Speed Sensor by "Cookie" Measurements

As used herein, "cookie" measurements refer to one technique of the invention for measuring speed. In this method, for example, the sensor drops a measurable entity—e.g., electronic charge—into the snow and then picks it up later at a known distance away to determine the speed. The "charge" in this example is the "cookie."

In skiing, therefore, this method involves dropping a cookie as the ski travels and then detecting the coolie at a known distance down the length of the ski. The time between placement and detection given a known length between the two occurrences will determine the speed. A cookie therefore represents the placement of some measurable characteristic into the snow underneath. This characteristic may be electrical charge, magnetic moments, a detectable material such as ink, perfume, or a radiation source. The cookies may be dropped at a constant rate, i.e. cookies per second, or at a fixed distance between cookies. In such cases the cookies are said to be dropped in a closed loop fashion. Also the amount of charge, magnetic moment, or detectable material may be controlled so that the detection occurs just above threshold. This will tend to minimize the amount of electrical power used and minimize the amount of material dispensed.

In FIGS. 19 and 19A, a snowboard 498 traveling in a direction 504 has two sets of electrodes attached to the ski. The first set of electrodes 503 is used to charge a small amount of snow 499 by applying an electric potential across terminals 501a and 501b. The potential in that snow 499 is then read by the set of electrodes 502, accomplished by sampling the potential between terminals 500a and 500b.

Since the level of charge in the snow 499 will be quite low, an instrumentation amplifier may be used to condition the signal, such as known to those skilled in the art. FIG. 19B shows the charge and detection loop according to the preferred embodiment. A potential source—e.g., a battery 499—is used to charge the first electrodes 503. When the output of the instrumentation amplifier 501 is above a predetermined threshold, the control and timing circuit 505 triggers a flip-flop (not shown) that notifies the microprocessor that the charge is detected. The time that transpired between placing the charge at 503 to detecting the charge at 502 is used to determine the speed the ski is traveling. The speed is simply the distance between the two sets of electrodes 503 to 502 divided by the time between setting and receiving the charge. The functionality of the timing and control circuit 505 can be separate or, alternatively, can be within the microprocessor such as described herein.

The second set of electrodes 502 that is used to detect the charge may also be used to clear the charge such as by driving a reverse voltage (from the control and timing circuit 505 and through direct circuitry to the electrodes 502). In this manner to total charge resulting from the ski traversing the field of snow will be zero so that there will be no charge pollution. Also it will not confuse another ski speed detection system according to the invention.

Figure 20:
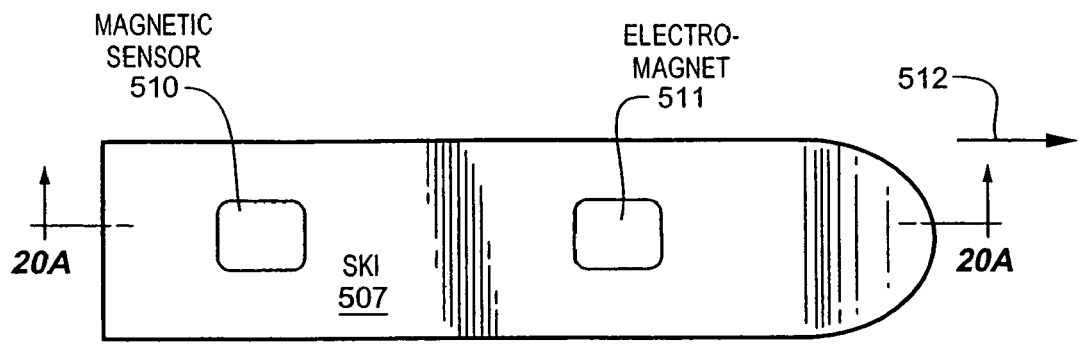
FIGS. 20 and 20A show another embodiment of the invention for determining speed through magnetic cookies.
Figure 20A:
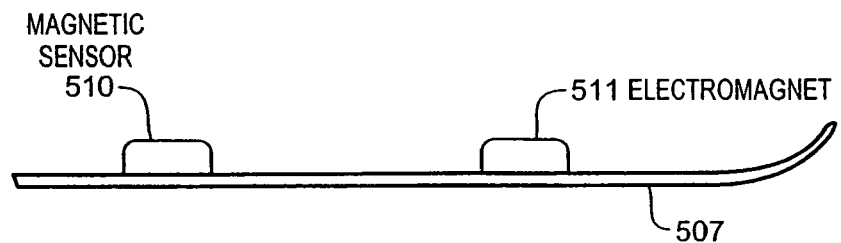

The situation described above is also applicable to magnetic moment cookies. In FIG. 20, for example, a ski 507 shown traveling in a direction 512 has an electromagnet 511 mounted on top of the ski 507 and a magnetic sensor 510. As the skier skis along the electromagnet is used to impress a magnetic moment into the snow and water that resides under the ski 507. This is done by asserting a strong magnetic field from the electromagnet 511 and through the ski for a short period of time. This polarization may then be detected by the magnetic sensor 510. The period of time it takes from creating the magnetic moment at 511 to detecting it at 510 may be used in determining the speed of the ski 507 (such as through control and timing circuitry such as described in connection with FIG. 19B). The magnetic sensor 510 may also be used to cancel the magnetic moment so that the total magnetic moment will be zero after the ski travels from placement through detection and removal.

Figure 21:
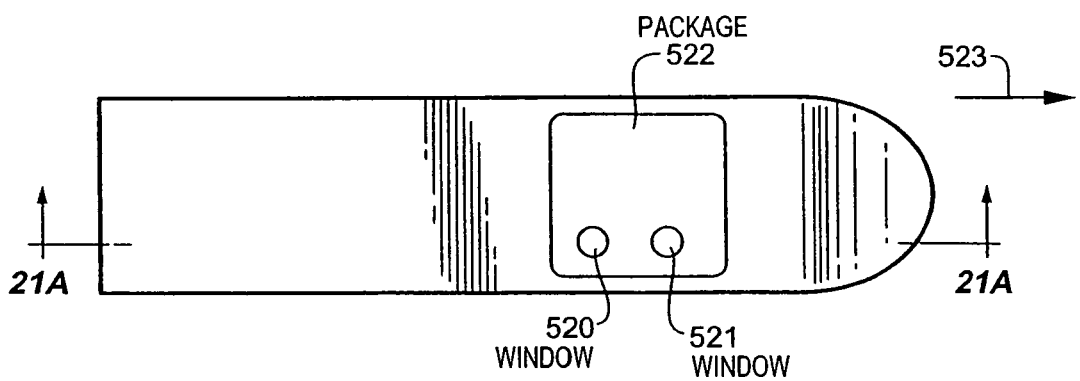
FIGS. 21 and 21A show yet another embodiment of determining speed through optical windows, according to the invention.
Figure 21A:
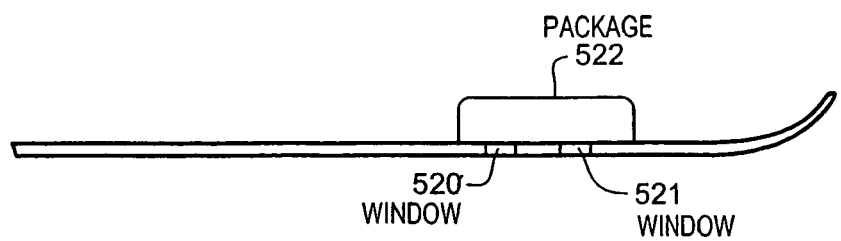

One other speed measurement system is shown in FIG. 21. Specifically, an optical correlation system is shown in FIG. 21 and includes a laser source and receiver contained in package 522. The laser is directed through two windows 520 and 521. The laser backscatter is cross correlated over time between the two windows 520, 521. This means that the two time signals are multiplied and integrated over all time with a fixed time delay between the two signals. The time delay between the two backscatter signals that yields the highest cross correlation is the period of time the ski took to travel the distance of the two windows. The speed of the ski may then be determined knowing the window separation. The source that is used does not have to be a laser but can be noncoherent visible light, infrared or any high frequency electromagnetic radiation.

The invention thus provides a series of unique sensing technologies which are appropriate for sporting activities such as skiing, snowboarding, windsurfing, skate-boarding, mountain biking, and roller-blading. Specifically, the invention is used to "sense," quantify and communicate to the user selected motions for various sporting activities. These motions include (A)–(C) below:

(1) Air Time

One embodiment of the invention—appropriately called the "airmeter" measures "air" time, i.e., the time for which a person such as a skier is off the ground, such as during a jump. The airmeter is battery-powered and includes a microprocessor and a low-powered liquid crystal display (LCD) to communicate the "air" time to the user. There are many ways the airmeter can "detect" the loft times associated with measuring "air" time; and certain techniques are better than others for various different sports. By way of example, certain of these airtime devices utilize accelerometers and/or microphone technology as part of the microprocessor circuit. All of the components for this device are cheap and plentiful; and are conveniently packaged within a single integrated circuit such as an ASIC.

The airmeter provides several features, including:
- total and peak air time for the day
- total dead time for the day
- air time for any particular jump
- successive jump records of air time
- averages and totals, selectable by the user
- rankings of records
- logic to reject activities which represents false "air" time
- toggle to other device functionality
- user interface to control parameters (2) Speed Certain of the sporting activities described above also benefit by the measurement of vehicle speed. Again, in the detection of this motion, one embodiment of the invention utilizes relatively simple and inexpensive technologies to sense, quantify and display vehicle speed. This device can be stand-alone, or it is incorporated within several of the other devices discussed herein. For example, one combination device will provide both "air" time and speed to the user of the device.

One method of determining speed utilizes the Doppler effect of microwave energy wherein energy transmits right through the vehicle, e.g., a ski or snowboard, and reflects off the moving ground to generate a Doppler signal. The absence of this signal is also used by PhatRat—in certain embodiments—to sense air time.

The speed measuring device of the invention provides several features, including:
- total average speed for the day
- peak speeds
- successive speed records
- averages and totals, selectable by the user
- rankings of records
- logic to reject activities which contaminate speed measurements
- toggle to other device functionality
- user interface to control parameters (3) "Power"

One embodiment of the invention also measures user "power," i.e., the amount of energy absorbed or experienced by a user during the day. By way of example, this "power" meter is useful for a kayaker in that it would assess and quantify the power or forces experienced by a white-water ride. One output of the power meter of the invention is the number of "g's" absorbed by the user.

Again, in the detection of power, the power meter utilizes relatively simple and inexpensive technologies to sense, quantify and display "g's" and/or other measures of how "hard" a user played in a particular activity. As above, this device can be stand-alone, or it is incorporated within several of the other devices discussed herein. For example, one combination device will provide "air" time, power and speed to the user of the device.

Figure 22:
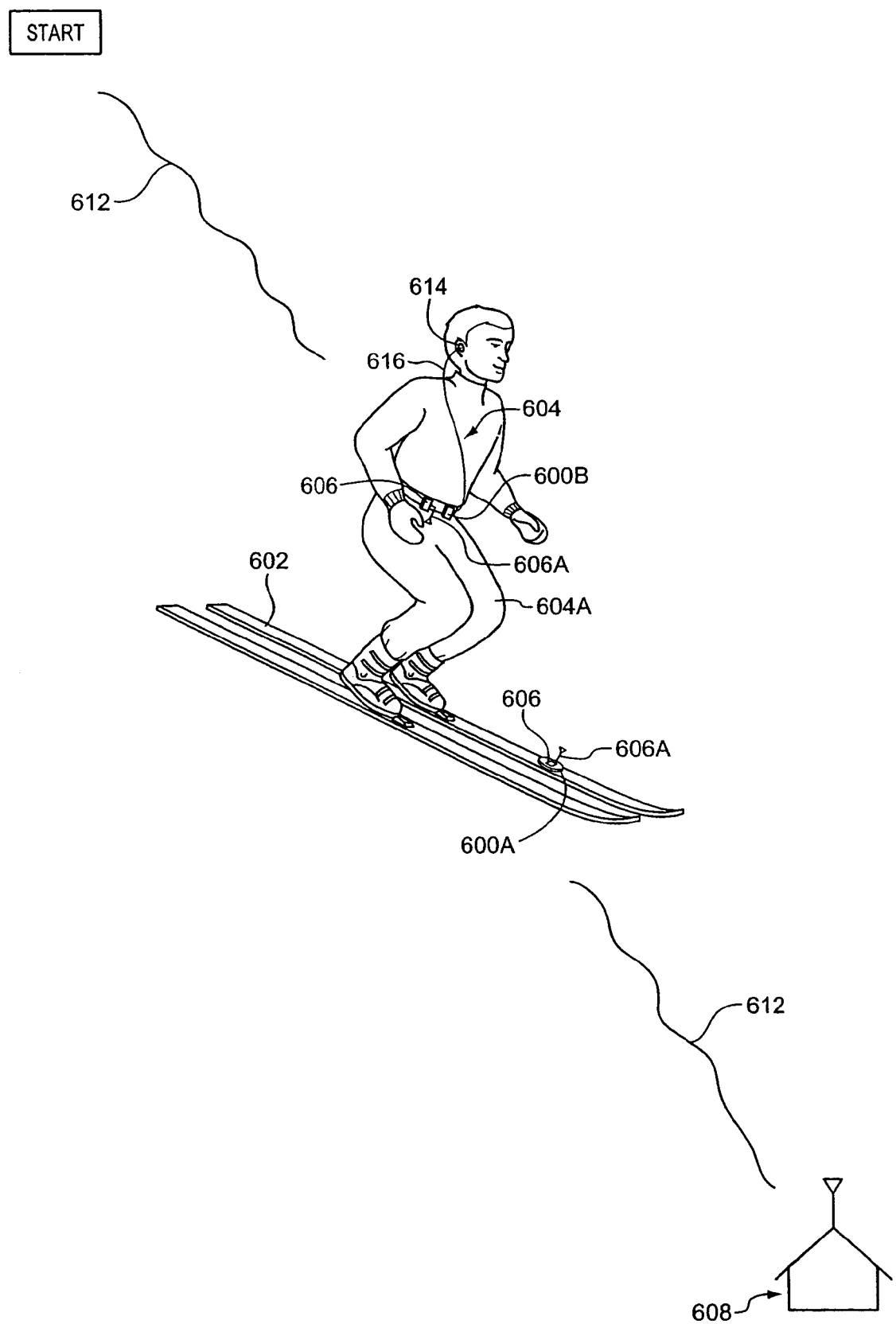
FIG. 22 shows a schematic view—not to scale—of a skier skiing down a mogul course and of system constructed according to the invention for monitoring two power meters to quantitatively measure mogul skiing performance relative to other skiers.

The power meter measuring device provides several features, including:
- average absorbed power
- peak power for the activity
- successive power records
- averages and totals, selectable by the user
- rankings of records
- logic to reject activities which contaminate power measurements
- toggle to other device functionality
- user interface to control parameters
- units control such as to display "g's" and/or other measures As shown in FIG. 22, a pair of power meters 600 is also used to quantify competitions such as mogul competitions. One power meter 600A mounts to the ski 602, and another power meter 600B mounts or attaches to the user's upper body 604; and an RF signal generator 606 communicates (via antenna 606a) the power information to a controller at a base facility 608 (e.g., a judges center for judging the mogul skiers). Those skilled in the art should appreciate that one or both power meters 600 can communicate the information to the base, as shown; however, one power meter can also communicate to the other power meter so that one communicates to the base. However, in either case, an RF transmitter and receiver is needed at each meter. Alternatively, other inter-power meter communication paths are needed, e.g., wiring, laser or IR data paths, and other techniques known to those in the art.

The combined signals from the meters 600 assess the force differential between the lower legs 604a and the upper body 604, giving an actual assessment of a competitor's performance. A computer at the base station 608 can easily divide one signal by the other to get a ratio of the two meters 600 during the run. The meters 600 start transmitting data at the starting gate 610 and continue to give data to the base 608 during the whole run on the slope 612. The meters can also be coupled to the user via a microphone 614 (and wire 616) to provide a hum or pitch which tells that user how effective his/her approach is. Although it is not shown, one or both meters have the microprocessor within so as to enable the features described in connection with the power meters. For example, the microprocessor can be used to provide a power measurement in "Gs" for the competitor once she reaches the base 608.

Other features can also be determined in accord with the invention such as through measurements with the system of FIG. 14A. For example, once you know your starting velocity, you can measure distance traveled and height above the ground by knowing the air time for a given jump.

Other ways of doing this are by using accelerometers to integrate the height distance. The preferred way of determining distance is to know your velocity at the jump start location, such as described herein, and to use the air time to establish a distance traveled, since distance is equal to velocity times time (or air time).

For height, you can also determine the height traveled by looking at the time to reach the ground. That is, once in the air, you are accelerating towards the ground at 9.81 meters per second ^2. So, you first determine the time for which there is no more upwards movement (such as by using an accelerometer that knows gravity direction and which changes directions at the peak, or by using circuitry which establishes this movement), and then calculate the distance traveled (in height) by knowing that the height is equal to ½ a t^2, where a is the acceleration of gravity (9.81 m/s^2) and t is the air time after the peak height is reached. If the person does not travel UP at any time during the jump, then the height is simply ½ a t^2 where t is the complete air time.

Figure 23:
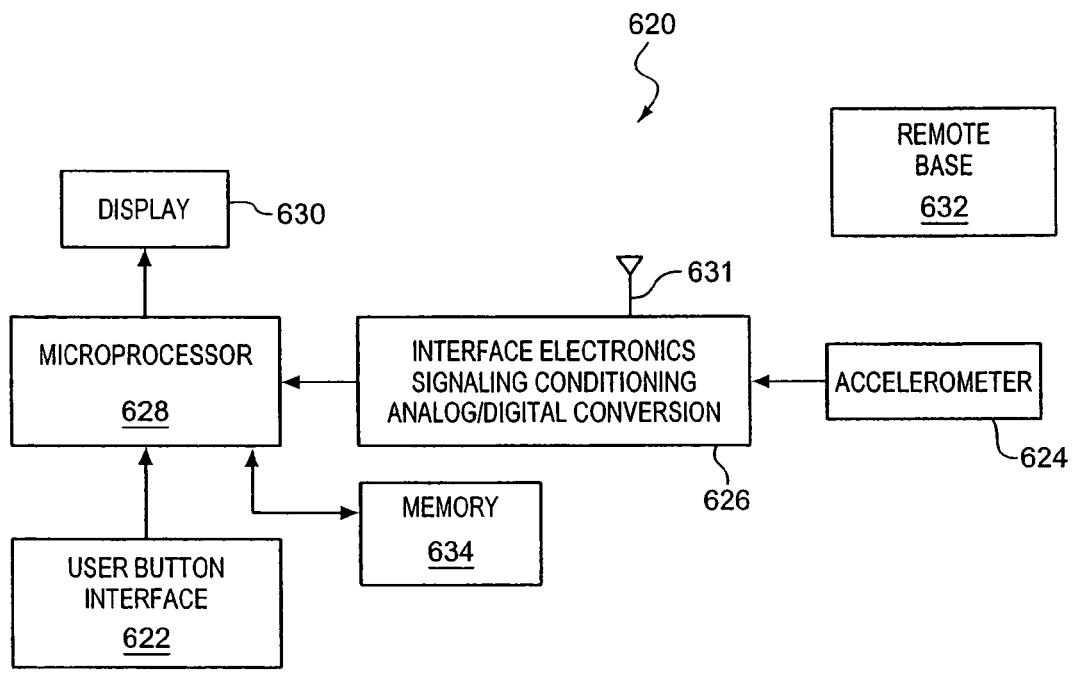
FIG. 23 shows a power meter constructed according to the invention for measuring activity energy for various sportsmen.

An accelerometer-based vibration and shock measurement system 620 is shown in FIG. 23. This system 620 measures and processes accelerations associated with various impact sports and records the movement so that the user can determine how much shock and vibration was endured for the duration of the event. The duration is determined with a simple start stop button 622, although duration can alternatively start with an automatic recording that is based on the measured acceleration floor.

The vibrations and shock associated with skiing or exercise are measured by the use of an accelerometer 624 (or other motion device, e.g., a microphone or piezoelectric device) and conditioning electronics 626 as shown in FIG. 23. The accelerometer 624 typically is AC-coupled so that low frequency accelerations, or the acceleration due to gravity, may be ignored. The accelerometer output is then conditioned by passing the signal through a band pass filter within the electronics 626 to filter out the low frequency outputs, such as the varying alignment to the gravity vector, as well as the high frequency outputs due to electrical noise at a frequency outside the performance of the accelerometer 624. The resulting signal is one that has no DC component and that is bipolar such as the waveform shown in FIG. 24.

Figure 24:
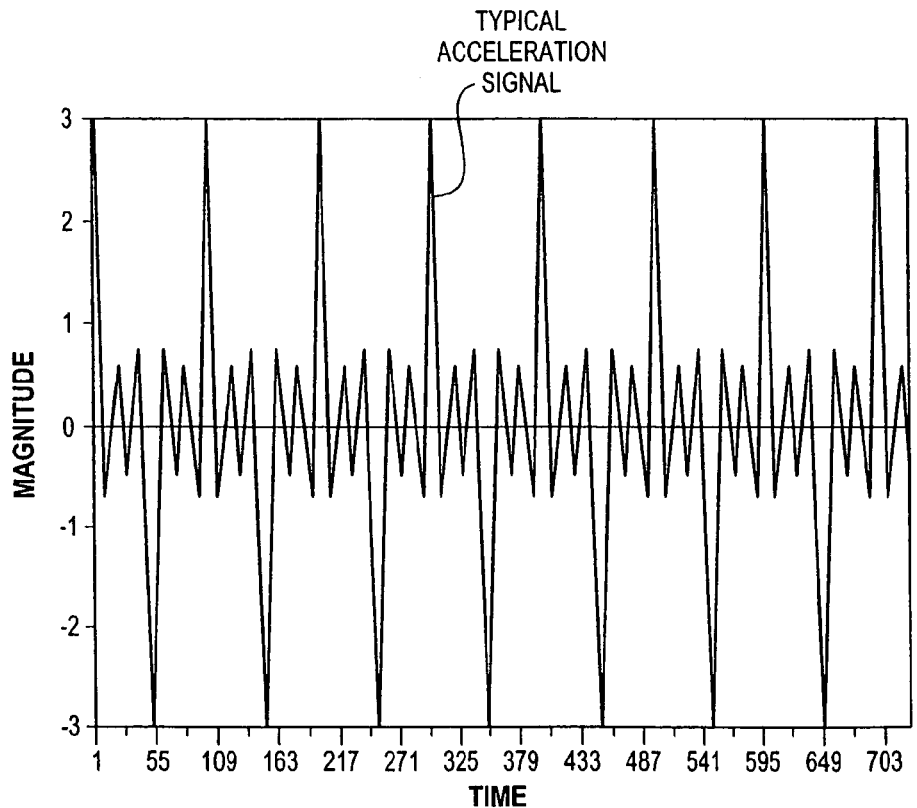
FIGS. 24–26 illustrate various, exemplary signals obtainable the power meter of FIG. 23.

The system 620 thus conditions the signal and remove the negative components of the waveform in FIG. 24. This is done, for example, by rectifying the output of the bandpass signal. Since a positive acceleration is likely to be accompanied by a negative of the same area, the area of the positive may be doubled to obtain the area of the positive and negative. The signal may also be processed by an absolute value circuit. This can be done via an Operational Amplifier circuit such as the one shown in the *National Semiconductor Linear Applications Data Book Application Note AN*-31., which is herein incorporated by reference. In accord with certain processes, known to those skilled in the art, positive values become positive; and negative values become positive. By way of example, the waveform of FIG. 24 is processed, for example, to the waveform of FIG. 25.

Figure 25:
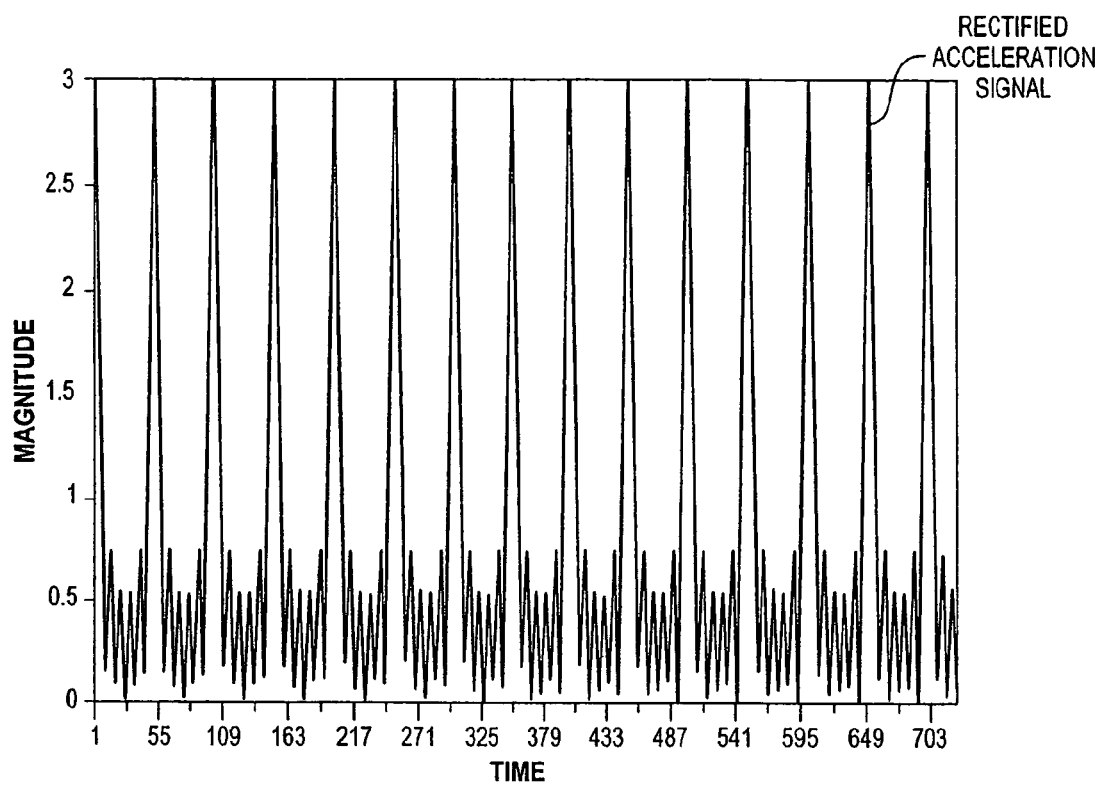
Figure 26:
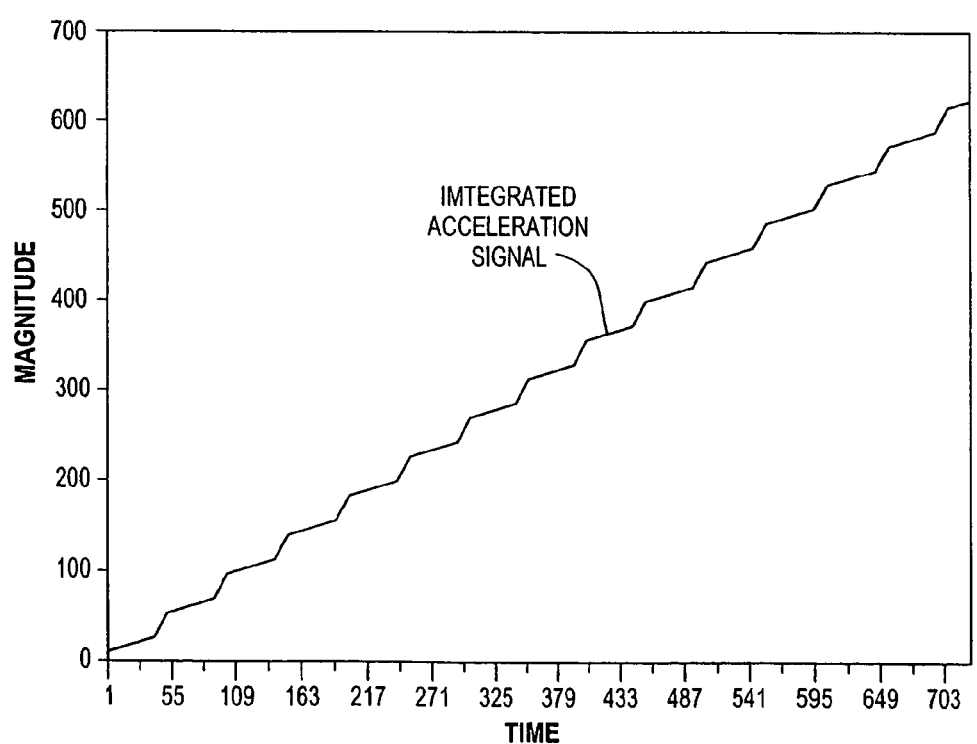

A unipolar waveform like the one shown in FIG. 25 is then integrated over time by the system 620 so that the total acceleration is accumulated. This can also be averaged to determine average shock. The signal of FIG. 25 is therefore processed through an integrator (within the electronics 626 or the microprocessor 628) which will result in the signal shown in FIG. 26. A value of "power" can then be displayed to a user via the display 630.

The period of integration may be a day or simply a single run down a slope; or it may be manually started and stopped at the beginning and end of a workout. The output is then be fed into a logarithmic amplifier so that the dynamic range may be compressed. The logarithmic amplifier can be accomplished within the microprocessor 628.

At any stage, the system 620 can be fed into an analog-to-digital converter (such as within the electronics 626) where the signal processing is done digitally. The output of the accelerometer 624 should anyway pass through an antialiasing filter before being read by a microprocessor 628. This filter is a low pass filter that will ensure that the highest frequency component in the waveform is less than half the sampling rate as determined by the Nyquist criteria.

The accelerometer 624 output can also be processed through an RMS circuit. The Root Mean Square acceleration is then determined from the following formula:

$$A_{RMS} = \frac{1}{T}\left[\int_0^T A^2(t)\partial t\right]^{1/2}$$

where T is the period of the measurement and A (t) is the instantaneous accelerometer output at any time t. The period T may be varied by the user and the output is a staircase where each staircase is of width T. This is then peak-detected and the highest RMS acceleration stored; and an average acceleration and a histogram are stored showing a distribution of RMS accelerations. These histograms are displayed on a Liquid Crystal graphical display 630, for example, as a bargraph.

An alternate embodiment is to record the signal in time and transform the signal to the frequency domain by performing a Fourier transformation to the data (such as within the electronics 626 or the microprocessor 628). The result would is distribution of the accelerations as a function of frequency which is then integrated to determine the total signal energy contained. The distribution is, again, plotted on the LCD display 630.

Data may also be acquired by the accelerometer and telemetered to the electronics 626 via an RF link 631 back to a remote location 632 for storage and processing. This enables ski centers to rent the accelerometer system 620 so as to be placed on the ski to record a day of runs and to give a printout at the end of the day.

A separate memory module or data storage device 634 can also be used to store a selected amount of time data which can be uploaded at the end of the day. The data can be uploaded itself via a Infrared link readily available off the shelf, as well as through a wire interface or through an RF link 631.

The system 620 is particularly useful in impact sports that include mountain biking, football, hockey, jogging and any aerobic activity. Low impact aerobics have become an important tool in the quest for physical fitness while reducing damage to the joints, feet and skeletal frames of the exerciser. The system 620 may also be used by a jogger to evaluate different running shoes. Alternatively, when calibrated, the system 620 is useful to joggers who can gate it to serve as a pedometer. The addition of a capacitor sensor in the heal electronics helps determine average weight. A sensor for skin resistivity may additionally be used to record pulse. The shoe can record the state of aerobic health for the jogger which is of significant interest to a person involved in regular exercise. The system 620 can also be used to indicate the gracefulness of a dancer while they develop a particular dance routine. A football coach may place these systems 620 in the helmets of the players to record vibration and shock and use it as an indicator of effort.

In skiing, the system 620 has other uses since a skier glides down a mountain slope and encounters various obstructions to a smooth flight. Obstructions such as moguls cause the skier to bump and induce a shock. This shock can be measured by the accelerometer 624 and accumulated in a memory 634 to keep a record of how muck shock was encountered on a particular ski run. Exercisers may use such a system 620 to grade their ability to avoid impact. A jogger may use the system 620 to evaluate their gate and determine their running efficiency. This becomes important with a greater emphasis being placed on low impact aerobics.

Those skilled in the art should appreciate that other improvements are possible and envisioned; and fall within the scope of the invention. For example, an accelerometer-based system 620 mounted on a ski may be used to determine the total shock and vibration encountered by a skier traveling down a slope. Mounting an additional accelerometer 624 above the skier's hip allows a measurement of the isolation the skier provides between upper torso and ski. This can be used to determine how well a trained a skier has become in navigating moguls. This measurement of the isolation is made by taking an average of the absolute value of the accelerations from both accelerometers 624. The ratio of the two accelerations is used as a figure of merit or the isolation index (i.e., the ratio between two measurements such as on the ski and the torso, indicating how well the mogul skier is skiing and isolating knee movement from torso movement).

To avoid the complications of gravity affecting the measurements of system 620, a high pass filter should be placed on the accelerometer output or within the digital processor sampling of the output. All analog signals should have antialiasing filters on their outputs whose bandwidth is half the sampling frequency. Data from the accelerometers 624 can sampled continuously while the circuits are enabled. The processor 628 may determine that a ski run has started by a rise in the acceleration noise floor above a preset trigger for a long enough duration. In another embodiment, a table is generated within the processor of each sufficiently high acceleration recorded from the ski. The corresponding upper torso measurement may also be recorded along with the ratio of the two measurements. The user can additionally display the n-bumpiest measurements taken from the skis and display the isolation index.

Figure 28:
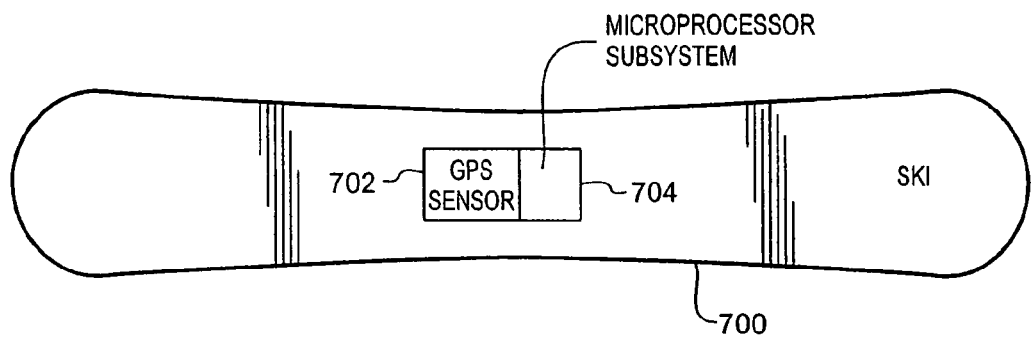
FIGS. 28 and 29 show alternative "air" measuring techniques, according to the invention.

FIG. 28 shows a ski 700 mounted with a GPS sensor 702 that is coupled to a microprocessor subsystem 704 such as described herein. The GPS sensor 702 tells absolute position in terms of height and earth location. By monitoring the signal from the GPS sensor 702, speed, height and loft time can be determined. That is, at each signal measurement, a difference is calculated to determine movement of the ski 700; and that difference can be integrated to determine absolute height off of the ground, distance traveled, speed (i.e., the distance traveled per sample period), and loft time.

Figure 29:
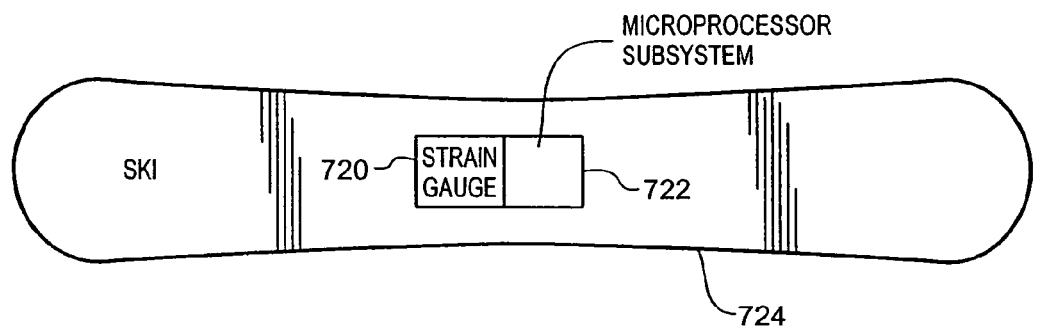

FIG. 29 shows a strain gauge 720 connected to a microprocessor subsystem 722 such as described above. The gauge 720 senses when there is little or now stress on the ski 724, such as when the ski 724 is in the "air"; and the subsystem 722 thus determines loft time from that relatively quiescent period.

Alternatively, the element 720 can be a temperature gauge that senses the change in temperature when the ski 724 leaves the ground. This change of temperature is monitored for duration until it again returns to "in contact" temperature. The duration is then equated to "loft time" or some calibrated equivalent (due to thermal impedance). Note that the impedance of air will be different from snow; and hence that change can be measured by the gauge 720 in this embodiment.

Figure 30:
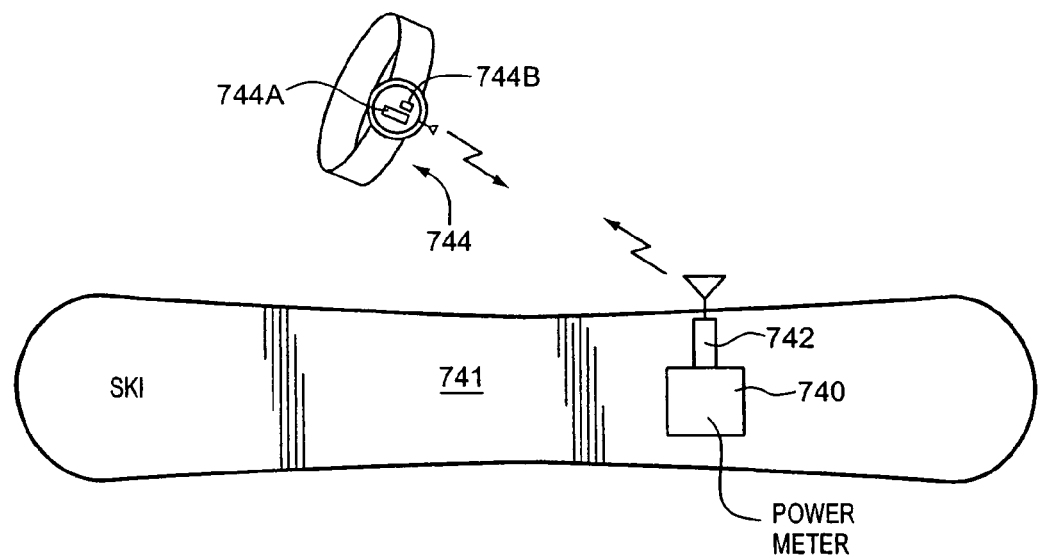
FIG. 30 shows a ski-to-watch transmitting system, constructed according to the invention, for informing a skier of performance factors at a watch rather than on the ski.

FIG. 30 shows one speed, loft and power meter 740, constructed according to the teachings herein and mounted to the ski 741, that additionally has an RF transmitter 742 to communicate signals from the meter 740 to a watch 744 worn by the user (not shown). In this manner, the user can easily look at the watch 744 (nearly during some sporting activities) to monitor the measured characteristics in near-real time. A small watch display 744a and internal memory 744b provide both display and storage for future review.

The devices for measuring speed, loft time and power as described herein can oftentimes be placed within another component such as a user's watch or a ski pole. For example, the power meter system 620 of FIG. 23 can easily be placed within a watch such as watch 744, and without the sensor 740, since power integration can be done from almost anywhere connected to the user. Likewise, loft time measurement through the absence of a spectrum, such as shown in FIG. 4, can also be done in a watch or a ski pole. Speed measurements, however, are much more difficult if not impossible to do at these locations because of the lack of certainty of the direction of movement. However, with the increased performance and size reductions of guidance systems with accelerometers (see FIGS. 14 and 14A), even this can be done.

Figure 31:
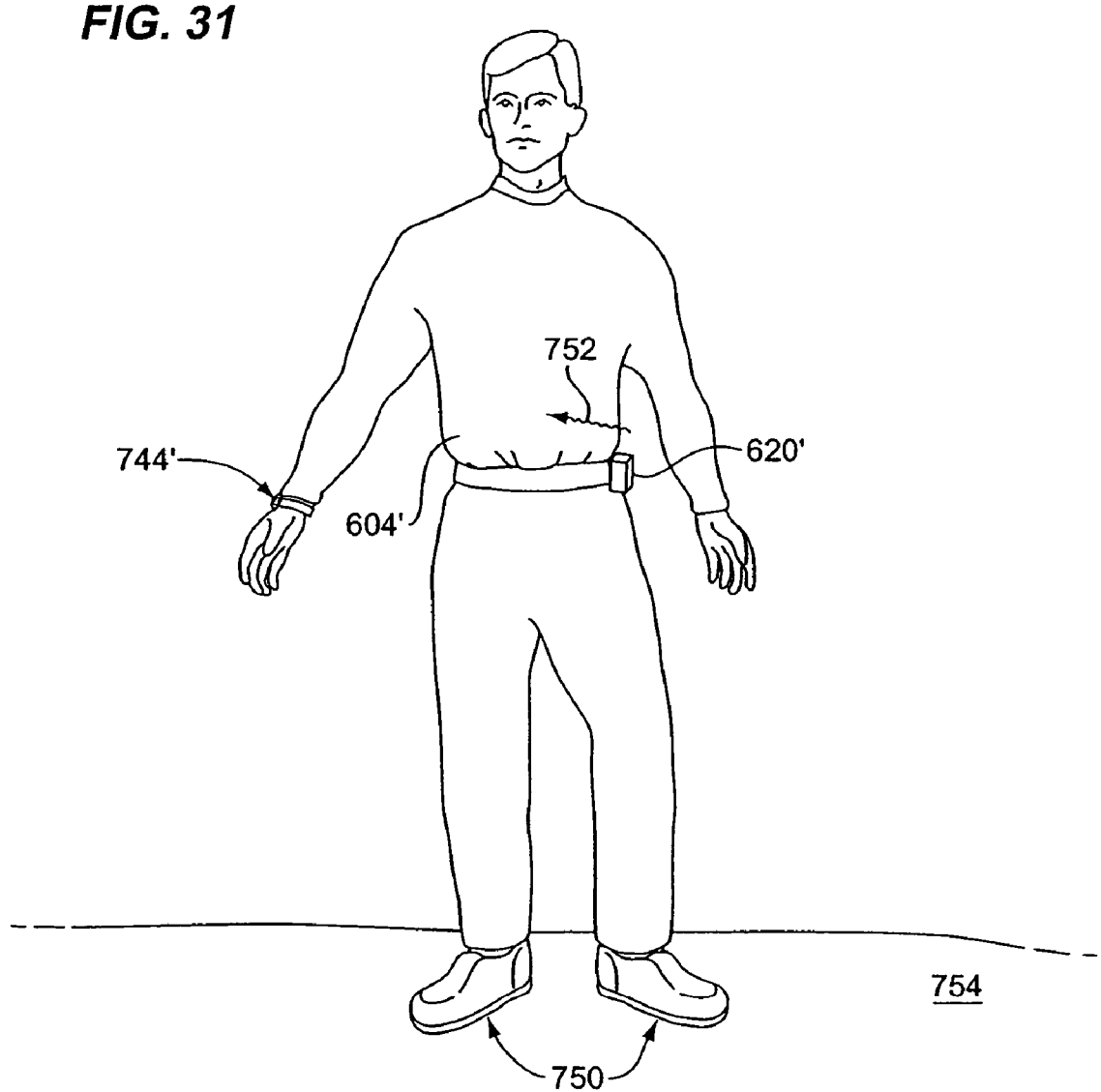
FIG. 31 Illustrates one system of the invention for evaluating stress and shoes in accord with the invention.

FIG. 31 shows a person 604' wearing a pair of shoes 750. A power meter 620' attaches to person 604' to communicate power information 752 to a receiver such as a wrist-watch 744'. Power meter 620' is for example similar to system 620, FIG. 22. Wrist-watch 744' is for example similar to watch 744, FIG. 30, such that information 752 is preferably a wireless data link between power meter 620' and watch 744'. In operation, power meter 620' quantifies motion associated with activity over ground 754 in view of a motion device (e.g., an accelerometer) within power meter 620'. By way of example, jarring motion perpendicular to ground 754 may be sensed by the accelerometer within power meter 620'. Accordingly, because shoes 750 cushion that jarring motion, power meter 620' may also be used to evaluate how effective shoes 750 are in shielding person 604' from jarring motion over ground 754.

It is accordingly intended that all matter contained in the above description or shown in the accompanying drawings be interpreted as illustrative rather than in a limiting sense.

It is also intended that the following claims cover all of the generic and specific features of the invention as described herein, and all statements of the scope of the invention which, as a matter of language, might be said to fall there between.

What is claimed is:

1. A system for determining sporting characteristics associated with a person during activity, comprising: at least one accelerometer and a processor contained within a protective housing for attachment to the person or to a vehicle ridden by the person, the accelerometer generating signals indicative of movement by the person, the processor processing the signals to determine the sporting characteristics, and further comprising an RF transmitter mounted within the housing for generating wireless signals indicative of the sporting characteristics, and a watch for receiving the wireless signals to display the sporting characteristics to the person.

2. A system of claim 1, the sporting characteristics comprising power.

3. A system of claim 1, the processor configured to determine the sporting characteristics as absorbed power experienced by the person during a time period of between about one-half second and eight hours.

4. A system of claim 1, the processor being calibrated to determine sporting characteristics as a pedometer for the person as a jogger.

5. A system for determining impact, comprising at least one accelerometer and a processor contained within a protective housing, the housing comprising at least part of a helmet of a football player, the accelerometer generating signals indicative of movement by the helmet, the processor being configured to process the signals to determine impact of the helmet, and further comprising a wireless transmitter configured with the housing to generate wireless signals indicative of the impact to a remote location.

6. A system of claim 1, the sporting characteristics comprising speed corresponding to movements of the person during the activity.

7. A system of claim 1, the sporting characteristics comprising power corresponding to movements of the person during the activity.

8. A system of claim 1, the sporting characteristics comprising distance traveled corresponding to movements of the person during the activity.

9. A system of claim 1, the sporting characteristics comprising drop distance corresponding to movements of the person during the activity.

10. A system for determining sporting characteristics associated with a person during activity, comprising: at least one accelerometer and a processor contained within a protective housing for attachment to the person or to a vehicle ridden by the person, the accelerometer generating signals indicative of movement by the person, the processor processing the signals to determine the sporting characteristics, and further comprising a wireless transmitter mounted within the housing for generating wireless signals indicative of the sporting characteristics, and a watch worn by the person for receiving the wireless signals to display the sporting characteristics to the person.

* * * * *